United States Patent
Winston et al.

(10) Patent No.: US 12,226,610 B2
(45) Date of Patent: Feb. 18, 2025

(54) TREATMENT OF PAIN ASSOCIATED WITH TOTAL KNEE ARTHROPLASTY WITH SUSTAINED-RELEASE LIPOSOMAL ANESTHETIC COMPOSITIONS

(71) Applicant: Pacira Pharmaceuticals, Inc., Parsippany, NJ (US)

(72) Inventors: Roy Winston, Parsippany, NJ (US); Mary DiGiorgi, Parsippany, NJ (US)

(73) Assignee: Pacira Pharmaceuticals, Inc., Parsippany, NJ (US)

( * ) Notice: Subject to any disclaimer, the term of this patent is extended or adjusted under 35 U.S.C. 154(b) by 0 days.

(21) Appl. No.: 18/104,979

(22) Filed: Feb. 2, 2023

(65) Prior Publication Data
US 2024/0148967 A1 May 9, 2024

Related U.S. Application Data

(60) Provisional application No. 63/422,146, filed on Nov. 3, 2022.

(51) Int. Cl.
*A61M 5/158* (2006.01)
*A61K 9/00* (2006.01)
(Continued)

(52) U.S. Cl.
CPC ........... *A61M 5/158* (2013.01); *A61K 9/0085* (2013.01); *A61K 9/127* (2013.01); *A61K 31/445* (2013.01); *A61M 5/427* (2013.01); *A61P 23/02* (2018.01)

(58) Field of Classification Search
CPC ..... A61M 5/158; A61M 5/427; A61K 9/0085; A61K 9/127; A61K 31/445; A61P 23/02
See application file for complete search history.

(56) References Cited

U.S. PATENT DOCUMENTS

| 5,316,771 A | 5/1994 | Barenholz |
| 5,817,074 A | 10/1998 | Racz |

(Continued)

FOREIGN PATENT DOCUMENTS

| CN | 103142458 | 6/2013 |
| CN | 106344521 | 1/2017 |

(Continued)

OTHER PUBLICATIONS

Tak R, Gurava Reddy AV, Jhakotia K, Karumuri K, Sankineani SR. Continuous adductor canal block is superior to adductor canal block alone or adductor canal block combined with IPACK block (interspace between the popliteal artery and the posterior capsule of knee) in postoperative analgesia and ambulation following total knee arthroplasty: randomized control trial. Musculoskelet Surg. Jun. 2022;106(2):155-162. doi: 10.1007/s12306-020-00682-8. Epub Sep. 27, 2020. PMID: 32980982.*

(Continued)

*Primary Examiner* — Theodore J Stigell
(74) *Attorney, Agent, or Firm* — Fish & Richardson P.C.

(57) ABSTRACT

In some embodiments provided herein are methods of administering an adductor canal block in a patient, wherein the methods include: (a) selecting an entry point of an injection needle in a leg of the patient; (b) inserting the injection needle into the leg of the patient at the entry point; (c) identifying a first nerve in the leg of the patient; (d) administering to the first nerve saline and a pharmaceutical composition; (e) identifying a second nerve in the leg of the patient; (f) administering to the second nerve saline and the pharmaceutical composition; wherein the first nerve and second nerve are selected from the group consisting of the nerve to vastus medialis (NVM) and the saphenous nerve, and wherein the first nerve is not the second nerve, and (Continued)

wherein the pharmaceutical composition comprises multi-vesicular liposomes.

28 Claims, 24 Drawing Sheets

(51) Int. Cl.
    *A61K 9/127*     (2006.01)
    *A61K 31/445*     (2006.01)
    *A61M 5/42*     (2006.01)
    *A61P 23/02*     (2006.01)

(56) References Cited

U.S. PATENT DOCUMENTS

| | | |
|---|---|---|
| 8,182,835 B2 | 5/2012 | Kim et al. |
| 8,410,104 B2 | 4/2013 | Brummett |
| 8,834,921 B2 | 9/2014 | Kim et al. |
| 8,906,966 B2 | 12/2014 | Sherwood et al. |
| 8,957,779 B2 | 2/2015 | Wu et al. |
| 8,975,268 B2 | 3/2015 | Berde et al. |
| 8,975,281 B2 | 3/2015 | Berde et al. |
| 9,192,575 B2 | 11/2015 | Kim et al. |
| 9,205,052 B2 | 12/2015 | Kim et al. |
| 9,585,838 B2 | 5/2017 | Hartounian et al. |
| 10,398,648 B2 | 9/2019 | Schutt et al. |
| 11,033,495 B1 | 1/2021 | Hall et al. |
| 11,179,336 B1 | 11/2021 | Hall et al. |
| 11,278,494 B1 | 3/2022 | Hall et al. |
| 11,304,904 B1 | 4/2022 | Hall et al. |
| 11,311,486 B1 | 4/2022 | Hall et al. |
| 11,357,727 B1 | 6/2022 | Hall et al. |
| 11,426,348 B2 | 8/2022 | Hall et al. |
| 11,452,691 B1 | 9/2022 | Hall et al. |
| 11,759,459 B2 | 9/2023 | Winston et al. |
| 11,812,358 B2 | 11/2023 | Slonin et al. |
| 11,819,572 B2 | 11/2023 | Los et al. |
| 11,819,573 B2 | 11/2023 | Slonin et al. |
| 11,918,565 B1 | 3/2024 | Winston et al. |
| 11,918,688 B2 | 3/2024 | Slonin et al. |
| 11,931,459 B2 | 3/2024 | Winston |
| 2002/0039596 A1 | 4/2002 | Hartounian et al. |
| 2003/0059462 A1 | 3/2003 | Barenholz |
| 2003/0069318 A1 | 4/2003 | Dang et al. |
| 2003/0152637 A1 | 8/2003 | Chasin et al. |
| 2003/0170288 A1 | 9/2003 | Carr et al. |
| 2006/0078606 A1* | 4/2006 | Kim ............... A61K 31/167 424/450 |
| 2007/0249681 A1 | 10/2007 | Sudo et al. |
| 2009/0105693 A1* | 4/2009 | Ben-David ........ A61B 17/3401 604/246 |
| 2009/0202436 A1 | 8/2009 | Hobot et al. |
| 2011/0250264 A1 | 10/2011 | Schutt et al. |
| 2012/0179038 A1 | 6/2012 | Meurer et al. |
| 2012/0294850 A1 | 11/2012 | Yu et al. |
| 2013/0177633 A1 | 7/2013 | Schutt et al. |
| 2013/0177634 A1 | 7/2013 | Schutt et al. |
| 2013/0177635 A1 | 7/2013 | Schutt et al. |
| 2013/0177636 A1 | 7/2013 | Schutt et al. |
| 2013/0177637 A1 | 7/2013 | Schutt et al. |
| 2013/0177638 A1 | 7/2013 | Schutt et al. |
| 2013/0183372 A1 | 7/2013 | Schutt et al. |
| 2013/0183373 A1 | 7/2013 | Schutt et al. |
| 2013/0183375 A1 | 7/2013 | Schutt et al. |
| 2013/0189349 A1 | 7/2013 | Kim et al. |
| 2013/0195965 A1 | 8/2013 | Schutt et al. |
| 2013/0306759 A1 | 11/2013 | Schutt et al. |
| 2013/0344132 A1 | 12/2013 | Kim et al. |
| 2014/0296293 A1 | 10/2014 | Andersen et al. |
| 2015/0250724 A1 | 9/2015 | Yamashita et al. |
| 2016/0000705 A1 | 1/2016 | McDonald et al. |
| 2016/0089335 A1 | 3/2016 | Ohri et al. |
| 2016/0361260 A1 | 12/2016 | Schutt et al. |
| 2016/0375140 A1 | 12/2016 | Ottoboni et al. |
| 2017/0007549 A1 | 1/2017 | Yum et al. |
| 2018/0092847 A1 | 4/2018 | Schutt et al. |
| 2019/0231762 A1 | 8/2019 | Verity |
| 2021/0205501 A1 | 7/2021 | Bright |
| 2021/0268271 A1 | 9/2021 | Bright |
| 2022/0015738 A1 | 1/2022 | Harbi et al. |
| 2022/0096116 A1* | 3/2022 | McFarland ........ A61B 10/0233 |
| 2022/0273564 A1 | 5/2022 | Slonin et al. |
| 2022/0218610 A1 | 7/2022 | Sionin |
| 2022/0218613 A1 | 7/2022 | Slonin et al. |
| 2022/0387318 A1 | 12/2022 | Winston |
| 2023/0038098 A1 | 2/2023 | Winston et al. |
| 2023/0042662 A1 | 2/2023 | Los et al. |
| 2023/0052319 A1 | 2/2023 | Winston et al. |
| 2023/0080593 A1 | 3/2023 | Winston et al. |
| 2023/0087140 A1 | 3/2023 | Winston et al. |
| 2023/0130180 A1 | 4/2023 | Los et al. |
| 2024/0058270 A1 | 2/2024 | Winston |

FOREIGN PATENT DOCUMENTS

| | | |
|---|---|---|
| CN | 108078929 | 5/2018 |
| CN | 109745607 | 5/2019 |
| CN | 110215435 | 9/2019 |
| RU | 2307675 | 10/2007 |
| WO | WO 1997/003652 | 2/1997 |
| WO | WO 1999/013865 | 3/1999 |
| WO | WO 1999/044640 | 9/1999 |
| WO | WO 2016/174661 | 11/2016 |
| WO | WO 2018/226732 | 12/2018 |
| WO | WO 2018/237109 | 12/2018 |
| WO | WO 2020/010123 | 1/2020 |
| WO | WO 2021/141956 | 7/2021 |
| WO | WO 2021/141959 | 7/2021 |
| WO | WO 2021/141963 | 7/2021 |
| WO | WO 2022/132650 | 6/2022 |
| WO | WO 2022/150708 | 7/2022 |
| WO | WO 2022/221452 | 10/2022 |

OTHER PUBLICATIONS

Adductor Canal Block: What Nerves Are We After?, uploaded on Oct. 2, 2020 by Regional Anesthesiology and Acute Pain Medicine. Retrieved from internet: https://www.youtube.com/watch?v=fE4U7JQa2f8.*

Adductor Canal Block, uploaded on Jan. 29, 2021 by RAUKvideos. Retrieved from internet: https://www.youtube.com/watch?v=DZLjNHkbMtl.*

Vij N, Newgaard O, Norton M, Tolson H, Kaye AD, Viswanath O, Urits I. Liposomal Bupivacaine Decreases Post-Operative Opioid Use after Anterior Cruciate Ligament Reconstruction: A Review of Level I Evidence. Orthop Rev (Pavia). Aug. 5, 2022;14(3):37159. doi: 10.52965/001c.37159. PMID: 35936807; PMCID: PMC9353693.*

Hadzic et al., "Liposome Bupivacaine Femoral Nerve Block for Postsurgical Analgesia after Total Knee Arthroplasty," Anesthesiology, Jun. 2016, 124(6):1372-1383.*

[No Author Listed] [online], "Full Prescribing Information—Exparel," exparel.com, revised Mar. 2022, retrieved on Apr. 14, 2022, retrieved from URL <https://www.exparel.com/hcp/prescribing-information.pdf?msclkid=60c82e5b2c231a2fdbe94c034f355fb2&utm_source=bing&utm_medium=cpc&utm_campaign=HCP%20-%20Branded&utm_term-exparel%20dosing%20information&utm_content=Dosage>, 36 pages.

Kim et al., "Preparation of multivesicular liposomes," Biochim. Biophys. Acta., Mar. 1983, 728(3):339-348.

Patel et al., "Brachial Plexus Block with Liposomal Bupivacaine for Shoulder Surgery Improves Analgesia and Reduces Opioid Consumption: Results from a Multicenter, Randomized, Double-Blind, Controlled Trial," Pain Med., 2020, 21(2):387-400.

Domb et al., "The effect of liposomal bupivacaine injection during total hip arthroplasty: a controlled cohort study," BMC Musculosketeal Disorders, 2014, 15(310):1-6.

Fiol et al., "Is There a Role for Liposomal Bupivacaine as Part of a Multimodal Strategy Inclusive of Intrathecarl Morphine for Post-Cesarean Analgesia? A Retrospective Chart Review Study," Anesth. Pain Res., 2020, 4(2):1-6.

(56) References Cited

OTHER PUBLICATIONS

Li et al., "Ultrasound-guided single popliteal sciatic nerve block is an effective postoperative analgesia strategy for calcaneal fracture: a randomized clinical trial," BMC Musculoskeletal Disorders, Jan. 2021, 22(735):1-9.
MayfieldClinic.com [online], "Epidural Steroid Injections (ESI)," Mayfield Brain & Spine, Jul. 2018, retrieved on May 9, 2023, retrieved from URL <https://d3djccaurgtij4.cloudfront.net/pe-esi.pdf>, 3 pages.
Rongstad et al., "Popliteal Sciatic Nerve Block for Postoperative Analgesia," Foot & Ankle International, Jul. 1996, 17(7):378-382.
Worrell et al., "The Mayo block: an efficacious block for hallux and first metatarsal surgery," AANA Journal, Apr. 1, 1996, 64(2):146-152, Abstract only.
[No Author Listed] [online], "Highlights of Prescribing Information—Exparel," accessdata.fda.gov, Apr. 2018, retrieved on Jun. 17, 2022, retrieved from URL <www.accessdata.fda.gov/drugsatfda_docs/label/2018/022496s9lbl.pdf>, 28 pages.
[No Author Listed] [online], "Marcaine [package insert]," accessdata.fda.gov, Oct. 2011, retrieved on Jun. 21, 2022, retrieved from URL <https://www.accessdata.fda.gov/drugsatfda_docs/label/2012/018692s015lbl.pdf>, 30 pages.
[No Author Listed] [online], "Naropin [package insert]," accessdata.fda.gov, Nov. 2018, retrieved on Jun. 21, 2022, retrieved from URL <https://www.accessdata.fda.gov/drugsatfda_docs/label/2018/020533s035lbl.pdf>, 30 pages.
Ahiskalioglu et al., "Can high volume pericapsular nerve group (PENG) block act as a lumbar plexus block?" Journal of Clinical Anesthesia, May 2020, 61:109650, 2 pages.
American Society of Anesthesiologists Task Force on Acute Pain Management, "Practice guidelines for acute pain management in the perioperative setting: an updated report by the American Society of Anesthesiologists Task Force on Acute Pain Management," Anesthesiology, Feb. 2012, 116(2):248-273.
American Society of Anesthesiologists, "ASA Physical Status Classification System," asahq.org, Dec. 13, 2020, retrieved from URL <https://www.asahq.org/standards-and-guidelines/asa-physical-status-classification-system>, 4 pages.
Beachler et al. "Liposomal bupivacaine in total hip arthroplasty: Do the results justify the cost?" Journal of Orthopaedics, 2017, 14:161-165.
Bigeleisen et al., "Novel approaches in pain management in cardiac surgery," Curr Opin Anaesthesiol. Feb. 2015, 28(1):89-94.
Biotechnology Innovation Organization "Standards for Future Opioid Analgesic Approvals and Incentives for New Therapeutics to Treat Pain and Addiction," Nov. 18, 2019, 11 pages.
Bronson et al. "Unanticipated transient sciatic nerve deficits from intra-wound liposomal bupivacaine injection during total hip arthroplasty," Arthroplasty Today, 2015, 1:21-24.
Chughtai et al., "Liposomal Bupivacaine Is Both Safe and Effective in Controlling Postoperative Pain After Spinal Surgery in Children: A Controlled Cohort Study," Clin Spine Surg., 2020, 33(10):E533-E538.
Cohen et al., "Incidence of adverse events attributable to bupivacaine liposome injectable suspension or plain bupivacaine for postoperative pain in pediatric surgical patients: A retrospective matched cohort analysis," Paediatr Anaesth., 2019, 29(2):169-174, 15 pages.
Day et al., "Extended Release Liposomal Bupivacaine Injection (Exparel) for Early Postoperative Pain Control Following Pharyngoplasty," J Craniofac Surg., Jul. 2018, 29(3):726-730, 4 pages.
De Leeuw et al., "The Psoas Compartment Block for Hip Surgery: The Past, Present, and Future," Anesthesiology Research and Practice, 2011, Article ID 159541, pp. 1-6.
Delgado et al., "Validation of Digital Visual Analog Scale Pain Scoring With a Traditional Paper-based Visual Analog Scale in Adults," J Am Acad Orthop Surg Glob Res Rev., Mar. 2018, 2(3):e088, 6 pages.
Duzlu et al., "Release Pattern of Liposomal Bupivacaine in Artificial Cerebrospinal Fluid," Turk J Anaesth Reanim., 2016, 44:1-6.
Ecoffey, "Refresher course: Local anesthetic pharmacology in children," Regional Anesthesia and Pain Medicine, 2015, 40(5):e23-e25.
FDA.gov [online] "Methodologies for Determining Opioid Sparing in Acute Pain Models," available on or before Dec. 14, 2019, via Internet Archive: Wayback Machine URL <http://web.archive.org/web/20191214114348/https://www.fda.gov/media/121206/download>, 61 pages.
Gan, "Poorly controlled postoperative pain: prevalence, consequences, and prevention," J Pain Res. 2017, 10:2287-2298.
Gerbershagen et al., "Pain intensity on the first day after surgery: a prospective cohort study comparing 179 surgical procedures," Anesthesiology, Apr. 2013, 118(4):934-944.
Ginosar et al., "ED50 and ED95 of Intrathecal Hyperbaric Bupivacaine Coadministered with Opioids for Cesarean Delivery," Anesthesiology, Mar. 2004, 100(3):676-682.
Giron Arango et al., "Reply to Dr Yu et al: Inadvertent quadriceps weakness following the pericapsular nerve group (PENG) block," Reg Anesth Pain Med, May 2019, 44(5):613-614.
Globalnewswire.com [online], "Pacira—Exparel Achieves Primary and Key Secondary Endpoints in Phase 4 Choice Study in Cesarean Section Patients," Jan. 7, 2020, retrieved on Apr. 11, 2022, retrieved from URL <https://www.globenewswire.com/news-release/2020/01/07/1967140/0/en/EXPAREL-Achieves-Primary-and-Key-Secondary-Endpoints-in-Phase-4-CHOICE-Study-in-Cesarean-Section-Patients.html>, 6 pages.
Gottschalk et al., "Quality of postoperative pain using an intraoperatively placed epidural catheter after major lumbar spinal surgery," Anesthesiology, Jul. 2004, 101(1):175-180.
Hu et al., "Pharmacokinetic profile of liposome bupivacaine injection following a single administration at the surgical site," Clin Drug Investig., 2013, 33(2):109-115.
International Preliminary Report on Patentability in International Appln. No. PCT/US2021/012266, dated Jul. 12, 2022, 14 pages.
International Preliminary Report on Patentability in International Appln. No. PCT/US2021/012269, mailed Jul. 21, 2022, 23 pages.
International Preliminary Report on Patentability in International Appln. No. PCT/US2021/012275, dated Jul. 12, 2022, 13 pages.
International Search Report and Written Opinion in International Appln. No. PCT/US2021/012266, dated Apr. 30, 2021, 16 pages.
International Search Report and Written Opinion in International Appln. No. PCT/US2021/012269, dated Mar. 25, 2021, 25 pages.
International Search Report and Written Opinion in International Appln. No. PCT/US2021/012275, dated Mar. 25, 2021, 14 pages.
International Search Report and Written Opinion in International Appln. No. PCT/US2022/011828, dated Apr. 1, 2022, 18 pages.
International Search Report and Written Opinion in International Appln. No. PCT/US2022/020713, dated Jun. 14, 2022, 24 pages.
Joshi et al., "The Safety of Liposome Bupivacaine Following Various Routes of Administration in Animals," Journal of Pain Research, 2015, 8:781-789.
Laura Giron-Arango et al., "Pericapsular Nerve Group (PENG) Block for Hip Fracture", Reg Anesth Pain Med, 2018, 43:859-863, 5 pages.
Li et al., "Acute postoperative opioid consumption trajectories and long-term outcomes in pediatric patients after spine surgery," J Pain Res., 2019, 12:1673-1684.
Malik et al., "Emerging roles of liposomal bupivacaine in anesthesia practice," Journal of Anaesthesiology Clinical Pharmacology, Apr.-Jun. 2017, 33(2):151-156.
Malinovsky et al., "Neurotoxicological Assessment After Intracisternal Injection of Liposomal Bupivacaine in Rabbits," Anesth. Analg., 1997, 85:1331-1336.
Manna et al., "Probing the mechanism of bupivacaine drug release from multivesicular liposomes," J Control Release, Jan. 28, 2019, 294:279-287, 41 pages.
Mannion et al., "In with the New, Out with the Old? Comparison of Two Approaches for Psoas Compartment Block," Anesthesia and Analgesia, 2005, 101:259-264.
Mannion, "Psoas Compartment Block," Continuing Education in Anaesthesia, Critical Care & Pain, 2007, 7(5):162-166.
Mazoit et al., "Pharmacokinetics of bupivacaine following caudal anesthesia in infants," Anesthesiology, Mar. 1, 1988, 68(3):387-391.

(56) References Cited

OTHER PUBLICATIONS

McGraw-Tatum et al. "A Prospective, Randomized Trial Comparing Liposomal Bupivacaine vs Fascia Iliaca Compartment Block for Postoperative Pain Control in Total Hip Arthroplasty," The Journal of Arthroplasty, 2017, 32:2181-2185.

Nedeljkovic et al., "Liposomal Bupivacaine Transversus Abdominis Plane Block for Pain After Cesarean Delivery: Results From a Multicenter, Randomized, Double-Blind, Controlled Trial," PowerPoint, Presented at Society for Obstetric Anesthesia and Perinatology 51st Annual Meeting, Phoenix, AZ, May 1-5, 2019, 17 pages.

Nedeljkovic et al., "Transversus Abdominis Plane Block With Liposomal Bupivacaine for Pain After Cesarean Delivery in a Multicenter, Randomized, Double-Blind, Controlled Trial," Anesth. Analg., Dec. 2020, 131(6):1830-1839.

Oda, "Pharmacokinetics and systemic toxicity of local anesthetics in children," Journal of anesthesia, Jun. 16, 2016, 30(4):547-550.

Peng et al., "Reply to Dr Nielsen: Pericapsular Nerve Group (PENG) block for hip fracture," Reg Anesth Pain Med, Mar. 2019, 44(3):415-416.

Perets et al. "Intraoperative Infiltration of Liposomal Bupivacaine vs Bupivacaine Hydrochloride for Pain Management in Primary Total Hip Arthroplasty: A Prospective Randomized Trial," The Journal of Arthroplasty, 2018, 33:441-446.

Rabbitts et al., "Presurgical psychosocial predictors of acute post-surgical pain and quality of life in children undergoing major surgery," J Pain., Mar. 2015, 16(3):226-234.

Rabbitts et al., "Trajectories of postsurgical pain in children: risk factors and impact of late pain recovery on long-term health outcomes after major surgery," Pain, Nov. 2015, 156(11):2383-2389.

Raja et al., "The revised International Association for the Study of Pain definition of pain: concepts, challenges, and compromises," PAIN, Sep. 1, 2020, 161(9):1976-1982.

Rice et al., "Pharmacokinetic Profile and Tolerability of Liposomal Bupivacaine Following a Repeated Dose via Local Subcutaneous Infiltration in Healthy Volunteers," Clin Drug Investig., 2017, 37(3):249-257.

Santos et al., "Is Continuous PENG Block the New 3-in-1?" J Anesth Clin Res 2019, Jun. 28, 2019, 10(6):1000898 , 2 pages.

Scott et al., "Acute Toxicity of Ropivacaine Compared with that of Bupivacaine," Anesthesia and Analgesia, Nov. 1, 1989, 69(5):563-569.

Shah et al., "Current Trends in Pediatric Spine Deformity Surgery: Multimodal Pain Management and Rapid Recovery," Global Spine J., 2020, 10(3):346-352.

Short et al., "Anatomic Study of Innervation of the Anterior Hip Capsule: Implication for Image-Guided Intervention," Regional Anesthesia and Pain Medicine, Feb. 2018, 43(2):186-192.

Springer et al., "Systemic Safety of Liposomal Bupivacaine in Simultaneous Bilateral Total Knee Arthroplasty," J Arthroplasty., Jan. 2018, 33(1):97-101.

Surdam et al., "The Use of Exparel (Liposomal Bupivacaine) to Manage Postoperative Pain in Unilateral Total Knee Arthroplasty Patients," Journal of Arthroplasty, 2015, 30:325-329.

Therapy Services Patient Information [online] "Pubic Rami Fracture," retrieved on Jan. 11, 2023, retrieved from URL <https://www.uhd.nhs.uk/uploads/about/docs/our_publications/patient_information_leaflets/orthopaedics/Pubic_rami_fracture.pdf>, 12 pages.

Tirotta et al., "Continuous incisional infusion of local anesthetic in pediatric patients following open heart surgery," Pediatr Anaesth., Jun. 2009, 19(6):571-576.

Tran et al.., "Is pericapsular nerve group (PENG) block a true pericapsular block?," Reg Anesth Pain Med, Feb. 2019, 44(2):257.

USFaD, "Pediatric Study Plans: Content of and Process for Submitting Initial Pediatric Study Plans and Amended Initial Pediatric Study Plans Guidance for Industry," US Food and Drug Administration, Jul. 2020, retrieved from URL <https://www.fda.gov/media/86340/download>, 26 pages.

Walker et al., "Complications in Pediatric Regional Anesthesia: An Analysis of More than 100,000 Blocks from the Pediatric Regional Anesthesia Network," Anesthesiology, Oct. 2018, 129(4):721-732.

www.sec.gov [online], "Pacira BioSciences Reports First Quarter 2019 Revenues of $91.3 Million," May 2019, retrieved on Sep. 30, 2022, retrieved from URL <https://www.sec.gov/Archives/edgar/data/1396814/000139681419000012/pcrx-3312019x991.htm>, 12 pages.

Yu et al., "Inadvertent quadriceps weakness following the pericapsular nerve group (PENG) block," Reg Anesth Pain Med, May 2019, 44(5):611-613.

Zel et al., "Neurological and Histological Outcomes After Subarachnoid Injection of a Liposomal Bupivacaine Suspension in Pigs: A Pilot Study," British Journal of Anaesthesia, Mar. 2019, 122(3):379-387.

Tong et al., "Liposomal bupivacaine and clinical outcomes," Best Practice & Research Clinical Anaesthesiology, 2014, 28:15-17.

Acharya et al., "Pericapsular Nerve Group Block: An Excellent Option for Analgesia for Positional Pain in Hip Fractures," Case Reports in Anesthesiology, Mar. 12, 2020, 2020,(1830136):1-3.

Ackmann et al., "Anatomy of the Infrapatellar Branch in Relation to Skin Incisions and as the Basis to Treat Neuropathic Pain by Percutaneous Cryodenervation," Pain Physician Journal, May/Jun. 2014, 17:E229-E348.

Bagaria et al., "The feasibility of direct adductor canal block (DACB) as a part of periarticular injection in total knee arthroplasty," Knee Surgery & Related Research, 2020, 32(48), 7 pages.

Chin et al., "Mechanisms of action of fascial plane blocks: a narrative review," Regional Anesthesia and Pain Medicine, 2021, 46:618-628.

Greenky et al., "Intraoperative Surgeon Administered Adductor Canal Blockade Is Not Inferior to Anesthesiologist Administered Adductor Canal Blockade: A Prospective Randomized Trial," The Journal of Arthroplasty, 2020, 35:1228-1232.

International Preliminary Report on Patentability in International Appln. No. PCT/US2022/011828, mailed on Jul. 20, 2023, 16 pages.

Matthews et al., "Surgeon-placed peripheral nerve block and continuous non-opioid analgesia in total knee arthroplasty is accessible intraoperatively: A cadaveric study," Journal of ISAKOS, Mar. 2023, 6 pages.

Matthews, "Continuous Adductor Canal & Periarticular Nerve Block for Total Knee Arthroplasty, Matthews' Placement Guide," Surgical Solutions, 2021, 6 pages.

Mont et al., "Can Joint Arthroplasty Surgeons Safely Administer Anesthesia?," The Journal of Arthroplasty, 2020, 35:1169.

Pepper et al., "Intraoperative Adductor Canal Block for Augmentation of Periarticular Injection in Total Knee Arthroplasty: A Cadaveric Study," The Journal of Arthroplasty, 2016, 31:2072-2076.

Peterson et al., "Surgeon-Performed High-Dose Bupivacaine Periarticular Injection with Intra-Articular Saphenous Nerve Block is Not Inferior to Adductor Canal Block in Total Knee Arthroplasty," The Journal of Arthroplasty, May 2020, 35:1233-1238.

Runge et al., "The Spread of Ultrasound-Guided Injectate From the Adductor Canal to the Genicular Branch of the Posterior Obturator Nerve and the Popliteal," Regional Anesthesia and Acute Pain, Dec. 2017, 42(6):725-730.

Sveom et al., "Ultrasound-Guided Adductor Canal Block Versus Intraoperative Transarticular Saphenous Nerve Block: A Retrospective Analysis," The Journal of Arthroplasty, 2022, 37:S134-S138.

Teachmeanatomy.info [online], "Anatomical Planes," Sep. 30, 2022, retrieved on Jun. 13, 2023, retrieved from URL <https://teachmeanatomy.info/the-basics/anatomical-terminology/planes/>, 2 pages.

Tran et al., "Evaluation of the proximal adductor canal block injectate spread: a cadaveric study," Reg. Anesth. Pain. Med., 2020, 45:124-130.

Yee et al., "Quadriceps Weakness After Single-Short Adductor Canal Block," The Journal of Bone and Joint Surgery, 2021, 103(1):30-36.

U.S. Appl. No. 17/684,805, Slonin et al., filed Mar. 20, 2022.
U.S. Appl. No. 17/719,716, Hall et al., filed Apr. 13, 2022.
U.S. Appl. No. 17/720,166, Hall et al., filed Apr. 13, 2022.
U.S. Appl. No. 17/840,104, Hall et al., filed Jun. 14, 2022.

(56) References Cited

OTHER PUBLICATIONS

U.S. Appl. No. 18/046,416, Garcia et al., filed Oct. 13, 2022.
U.S. Appl. No. 18/325,924, Hall et al., filed May 30, 2023.
U.S. Appl. No. 18/325,927, Hall et al., filed May 30, 2023.
Epstein et al., "Plasma Bupivacaine Concentrations Following lioinguinal-lliohypogastric Nerve Blockade in Children," Anesthesiology, Nov. 1, 1988, 69(5):773-776.
International Preliminary Report on Patentability in International Application No. PCT/US2022/020713, mailed on Sep. 28, 2023, 18 pages.
Kanazi et al., "The Analgesic Efficacy of Subarachnoid Morphine in Comparison with Ultrasound-Guided Transversus Abdominis Plane Block After Cesarean Delivery a Randomized Controlled Trial," Anesthesia & Analgesia, August 201, 111(2):475-481.
Medilogbiohealth.com [online], "Angles of Administration of Injection—ID, IM, SC, IV," Mar. 10, 2021, retrieved on Aug. 22, 2023, retrieved from URL <https://www.medilogbiohealth.com/2021/03/injection.html>, 8 pages.
Regional Anesthesiology and Acute Pain Medicine [online], "Adductor Canal Block: What Nerves Are We After?," uploaded on Oct. 2, 2020, retrieved from URL <https://www.youtube.com/watch?v=fE4U7JQa2f>, 9 pages.
Stow et al., "Plasma bupivacaine concentrations during caudal analgesia and ilioniguinal-iliohypogastric nerve block in children," Anaesthesia, Aug. 1998, 43(8):650-653.
U.S. Appl. No. 18/104,970, Winston et al., filed Feb. 2, 2023.
U.S. Appl. No. 18/239,587, Winston, filed Aug. 29, 2023.
U.S. Appl. No. 18/422,855, Winston et al., filed Jan. 25, 2024.
U.S. Appl. No. 18/425,917, Slonin et al., filed Jan. 29, 2024.
U.S. Appl. No. 18/606,084, Winston, filed Mar. 15, 2024.
U.S. Appl. No. 18/678,595, Dysart et al., filed May 30, 2024.
Baker et al., "Transversus abdominis plane block with liposomal bupivacaine for pain control after cesarean delivery: a retrospective chart review," Journal of Pain Research, Dec. 10, 2018, 11:3109-3116.
European Extended Search Report in European Application No. 21738517.8, dated Dec. 19, 2023, 10 pages.
European Extended Search Report in European Application No. 21738669.7, dated Dec. 13, 2023, 10 pages.
European Extended Search Report in European Application No. 21738912.1, dated Dec. 19, 2023, 12 pages.
Ilfield, "Liposome bupivacaine in peripheral nerve blocks and epidural injections to manage postoperative pain," Expert Opin. Phamacother., Oct. 23, 2013, 14(17):2421-2431.
International Search Report and Written Opinion in International Application No. PCT/US2023/036688, mailed on Mar. 13, 2024, 13 pages.
International Search Report and Written Opinion in International Application No. PCT/US2023/036694, mailed on Mar. 25, 2024, 24 pages.
Invitation to Pay Additional Fees and, Where Applicable, Protest Fee in International Application No. PCT/US2023/036688, mailed on Jan. 26, 2024, 3 pages.
Invitation to Pay Additional Fees and, Where Applicable, Protest Fee in International Application No. PCT/US2023/036694, mailed on Jan. 3, 2024, 2 pages.
Jansen et al., "Will the Addition of a Sciatic Nerve Block to a Femoral Nerve Block Provide Better Pain Control Following Anterior Cruciate Ligament Repair Surgery?" AANA Journal, Jun. 2009, 77(3):213-218.
Shevlin et al., "The Sciatic Nerve Block," BJA Education, Jul. 20, 2020, 20(9):312-320.
Tong et al., "Liposomal Bupivacaine and its Clinical Applications," Best Practice & Research Clinical Anaesthesiology, Dec. 31, 2014, 1-29.
Viscusi et al., "The Pharmacokinetics and Pharmacodynamics of Liposome Bupivacaine Administered via a Single Epidural Injection to Healthy Volunteers," Regional Anesthesia and Pain Medicine, Nov. 2012, 37(6):616-622.

* cited by examiner

Table 1 Summary of Demographics (Efficacy Analysis Set)

|  | Cohort 1 | | | Cohorts 1 + 2 | | |
|---|---|---|---|---|---|---|
|  | EXP-133-ADMIX (N = 24) | BUP50 (N = 21) | Subtotal (N = 45) | EXP-133-ADMIX (N = 85) | BUP50 (N = 81) | Total (N = 166) |
| Age (years), n | 24 | 21 | 45 | 85 | 81 | 166 |
| Mean (SD) | 61.92 (6.534) | 61.57 (8.675) | 61.76 (7.520) | 62.00 (7.049) | 62.21 (8.402) | 62.10 (7.716) |
| Median (Min, max) | 61.50 (51.0, 75.0) | 63.00 (45.0, 80.0) | 62.00 (45.0, 80.0) | 62.00 (44.0, 75.0) | 62.00 (37.0, 83.0) | 62.00 (37.0, 83.0) |
| Age category, n (%) | | | | | | |
| <45 years | 0 | 0 | 0 | 1 (1.2) | 2 (2.5) | 3 (1.8) |
| 45 to <65 years | 15 (62.5) | 15 (71.4) | 30 (66.7) | 53 (62.4) | 51 (63.0) | 104 (62.7) |
| ≥65 years | 9 (37.5) | 6 (28.6) | 15 (33.3) | 31 (36.5) | 28 (34.6) | 59 (35.5) |
| Sex, n (%) | | | | | | |
| Male | 12 (50.0) | 13 (61.9) | 25 (55.6) | 43 (50.6) | 42 (51.9) | 85 (51.2) |
| Female | 12 (50.0) | 8 (38.1) | 20 (44.4) | 42 (49.4) | 39 (48.1) | 81 (48.8) |
| Ethnicity, n (%) | | | | | | |
| Not Hispanic or Latino | 16 (66.7) | 17 (81.0) | 33 (73.3) | 64 (75.3) | 66 (81.5) | 130 (78.3) |
| Hispanic or Latino | 8 (33.3) | 3 (14.3) | 11 (24.4) | 21 (24.7) | 12 (14.8) | 33 (19.9) |
| Not reported | 0 | 1 (4.8) | 1 (2.2) | 0 | 3 (3.7) | 3 (1.8) |
| Race, n (%) | | | | | | |
| White | 21 (87.5) | 19 (90.5) | 40 (88.9) | 67 (78.8) | 63 (77.8) | 130 (78.3) |
| Black/African American | 2 (8.3) | 2 (9.5) | 4 (8.9) | 14 (16.5) | 15 (18.5) | 29 (17.5) |
| Other | 1 (4.2) | 0 | 1 (2.2) | 4 (4.7) | 3 (3.7) | 7 (4.2) |
| Other/Multiple/Not Reported/Unknown | 1 (4.2) | 0 | 1 (2.2) | 3 (3.5) | 1 (1.2) | 4 (2.4) |
| American Indian/Alaskan Native | 0 | 0 | 0 | 0 | 1 (1.2) | 1 (0.6) |
| Asian | 0 | 0 | 0 | 1 (1.2) | 0 | 1 (0.6) |
| Native Hawaiian or Pacific | 0 | 0 | 0 | 0 | 1 (1.2) | 1 (0.6) |

Abbreviations: Max = maximum; Min = minimum; SD = standard deviation.

FIG. 3

Table 2 Summary of Baseline Characteristics (Efficacy Analysis Set)

| | Cohort 1 | | | Cohorts 1 + 2 | | |
|---|---|---|---|---|---|---|
| | EXP133-ADMIX (N = 24) | BUP50 (N = 21) | Subtotal (N = 45) | EXP133-ADMIX (N = 85) | BUP50 (N = 81) | Total (N = 166) |
| ASA classification, n (%) | | | | | | |
| 1 | 6 (25.0) | 4 (19.0) | 10 (22.2) | 21 (24.7) | 21 (25.9) | 42 (25.3) |
| 2 | 18 (75.0) | 16 (76.2) | 34 (75.6) | 62 (72.9) | 56 (69.1) | 118 (71.1) |
| 3 | 0 | 0 | 0 | 2 (2.4) | 3 (3.7) | 5 (3.0) |
| Unknown | 0 | 1 (4.8) | 1 (2.2) | 0 | 1 (1.3) | 1 (0.6) |
| BMI (kg/m²), n | 24 | 21 | 45 | 84 | 81 | 165 |
| Mean (SD) | 32.53 (5.047) | 33.26 (4.756) | 32.87 (4.871) | 31.48 (4.795) | 32.74 (4.955) | 32.10 (4.900) |
| Median (Min, max) | 31.35 (22.9, 39.1) | 33.20 (24.1, 39.7) | 31.60 (22.9, 39.7) | 31.35 (19.2, 39.2) | 33.20 (22.8, 40.3) | 32.00 (19.2, 40.3) |
| BMI category, n (%) | | | | | | |
| <25 kg/m² | 1 (4.2) | 1 (4.8) | 2 (4.4) | 5 (5.9) | 7 (8.6) | 12 (7.2) |
| 25 to <30 kg/m² | 9 (37.5) | 3 (14.3) | 12 (26.7) | 31 (36.5) | 14 (17.3) | 45 (27.1) |
| ≥30 kg/m² | 14 (58.3) | 17 (81.0) | 31 (68.9) | 48 (56.5) | 60 (74.1) | 108 (65.1) |
| Unknown | 0 | 0 | 0 | 1 (1.2) | 0 | 1 (0.6) |
| Worst pain intensity[1] (NRS), n | 24 | 21 | 45 | 85 | 81 | 166 |
| Mean (SD) | 7.33 (1.993) | 7.14 (2.351) | 7.24 (2.144) | 7.22 (2.026) | 7.40 (2.322) | 7.31 (2.171) |
| Median (Min, max) | 8.00 (3.0, 10.0) | 8.00 (1.0, 10.0) | 8.00 (1.0, 10.0) | 8.00 (2.0, 10.0) | 8.00 (0.0, 10.0) | 8.00 (0.0, 10.0) |
| Average pain intensity[1] (NRS), n | 24 | 21 | 45 | 85 | 81 | 166 |
| Mean (SD) | 5.25 (2.770) | 4.86 (2.056) | 5.07 (2.444) | 5.16 (2.324) | 5.27 (2.219) | 5.22 (2.267) |
| Median (Min, max) | 5.00 (0.0, 10.0) | 5.00 (1.0, 8.0) | 5.00 (0.0, 10.0) | 5.00 (0.0, 10.0) | 5.00 (0.0, 10.0) | 5.00 (0.0, 10.0) |

Abbreviations: ASA = American Society of Anesthesiologists; BMI = body mass index; Max = maximum; Min = minimum; NRS = Numeric Rating Scale; SD = standard deviation.
1. In the last 30 days.

FIG. 4

| | Screening Visit[1] | Day of Surgery (Prior to Surgery) | OR | PACU | \multicolumn{14}{c}{Time from End of Surgery (h)} | Health Care Facility Discharge[2] | POD 14 Call ±3 days |
| --- | --- | --- | --- | --- | --- | --- | --- | --- | --- | --- | --- | --- | --- | --- | --- | --- | --- | --- | --- | --- |
| | | | | | 6 ±2 | 12 ±2 | 18 ±2 | 24 ±2 | 30 ±2 | 36 ±2 | 42 ±2 | 48 ±2 | 54 ±2 | 60 ±2 | 66 ±2 | 72 ±2 | 78 ±3 | 84 ±3 | 90 ±3 | 96 ±3 | | |
| Obtain ICF* | X | | | | | | | | | | | | | | | | | | | | | |
| Assess/confirm eligibility* | X | X[3] | | | | | | | | | | | | | | | | | | | | |
| Record medical/surgical history*[4] | X | | | | | | | | | | | | | | | | | | | | | |
| Collect height/weight for BMI calculation* | X | | | | | | | | | | | | | | | | | | | | | |
| Demographics and baseline characteristics* | X | | | | | | | | | | | | | | | | | | | | | |
| Record prior and concomitant Medications[4] | X | X[3] | | | | | | | | | | | | | | | | | | | | |
| Urine pregnancy test for WOCBP | X | X[3] | | | | | | | | | | | | | | | | | | | | |
| Urine drug screen | | X[3] | | | | | | | | | | | | | | | | | | | | |
| Review pain Rating Guide | | X[3] | | | | | | | | | | | | | | | | | | | | |
| Record worst and average pain (NRS) in the last 30 days | | X[3] | | | | | | | | | | | | | | | | | | | | |
| Randomize subject; prepare study drug | | X | | | | | | | | | | | | | | | | | | | | |
| Record block start/end times[5] | | X | | | | | | | | | | | | | | | | | | | | |
| Capture ultrasound video for the nerve block and send to Sponsor | | X | | | | | | | | | | | | | | | | | | | | |
| Record IPACK start/end times | | X | | | | | | | | | | | | | | | | | | | | |
| Record surgery start and end times | | | X | | | | | | | | | | | | | | | | | | | |

FIG. 5

| | Screening Visit[1] | Day of Surgery (Prior to Surgery) | OR | PACU | Time from End of Surgery (h) | | | | | | | | | | | | | | | | Health Care Facility Discharge[2] | POD 14 call ±3 days |
|---|---|---|---|---|---|---|---|---|---|---|---|---|---|---|---|---|---|---|---|---|---|---|---|
| | | | | | 6 ±2 | 12 ±2 | 18 ±2 | 24 ±2 | 30 ±2 | 36 ±2 | 42 ±2 | 48 ±2 | 54 ±2 | 60 ±2 | 66 ±2 | 72 ±2 | 78 ±3 | 84 ±3 | 90 ±3 | 96 ±3 | | |
| Record intra-op medication administered | | | X | | | | | | | | | | | | | | | | | | | |
| Record Pre-op and post-op scheduled analgesic medication[6] | | X | ↓ | | | | | | | | | | | | | | | | | | → | |
| Record PACU time in and out | | | | X | | | | | | | | | | | | | | | | | | |
| Record scheduled NRS scores[7,8] | | | | | X | X | X | X | X | X | X | X | X | X | X | X | X | X | X | X | | |
| Record worst and average NRS scores (24-hour recall)[7,8] | | | | | | | | X | | | | X | | | | X | | | X | X | | |
| Record unscheduled NRS immediately prior to breakthrough pain medication[9] | | | ↓ | | | | | | | | | | | | | | | | | ↑ | | |
| Record breakthrough pain medication[9] | | | ↓ | | | | | | | | | | | | | | | | | ↑ | | |
| Record day and time of HCF admission and discharge | | X | | | | | | | | | | | | | | | | | | | X | |
| Record AEs/SAEs[10] | ↓ | | | | | | | | | | | | | | | | | | | | | ↑ |
| Subject's satisfaction questionnaire (IPO) | | | | | | | | | | | | | | | | | | | | X | | |

Abbreviations: AE=adverse event; BMI=Body mass index; h=hours(s); HCF=health care facility; ICF=informed consent form; IPO=International pain outcome; min=minute(s); NRS=numeric rating scale; NSAID=nonsteroidal anti-inflammatory drug; OR=Operating room; PACU=Post-Anesthesia Care Unit; POD=Post-operative day; SAE=serious adverse event; WOCBP=women of childbearing potential.
* No more than 45 days before scheduled surgery day
1. Subjects may be screened on the same day as health care facility admission/surgery (with ample time for the informed consent process) or up to 45 days prior to surgery, but eligibility will be re-confirmed on the day of surgery prior to randomization. Screening procedures that are standard of care at the institution may be completed prior to written informed consent. Any screening procedures that are not SOC must be completed after written informed consent is obtained.

FIG. 5 (Cont.1)

2. Subjects in Cohort 1 and Cohort 2 will be discharged after 168 h and 96 h assessments, respectively.
3. Eligibility criteria, prior medication, urine pregnancy test, and urine drug screen to be assesed prior to randomization; review of Pain Rating Guide and worst and average pain scores over the previous 30 days to be assessed prior to study drug administration.
4. Relevant medical/surgical history within the last 5 years (including all ongoing history, regardless of start date) should be recorded, with the exception of history that is relevant to the TKA surgery, in which case all years should be recorded. Prior medications taken within 30 days of randomization (including all ongoing medications, regardless of start date) will be recorded.
5. Block to be administered 90 min (±30 min) prior to surgery.
6. Record all pre-operative and post-operative scheduled analgesic medication (celecoxib and acetaminophen)
7. The NRS pain intensity assessment should not be completed after any physical activity, including the motor block assessment (for Cohort 1 subjects). If that is not possible, to assess pain intensity at rest, the subject should rest quietly in a supine or seated position that does not exacerbate subject's postsurgical pain for 5-10 minutes before assessing the pain score using the NRS. If a subject is asleep, the subject will not be awakened to assess pain. If the subject awakens within the assessment window, a pain score will be collected then.
8. Pain scores (24 hr recall) once daily (i.e., worst/average pain) will be collected at 24 (±2 h), 48 (±2 h), 72 (±2 h), and 96 (±3 h) post-surgery. Pain scores (current pain) will be collected by the study staff beginning at PACU admission (±5 min); q15 min in PACU (±5 min); at PACU discharge (±5 min) ; then q6h (±2 h) from end of surgery to 72 hours post-surgery and q6h (±3 h) from 78-96 hours post-surgery.
9. Oxycodone will be administered on an as needed (PRN) basis for breakthrough pain through 96 hours post-surgery; opioids should not be given on a pre-determined schedule.
   Immediate release oral (PO) oxycodone will be administered in a stepwise approach:
   * Initial dose of 5 mg oxycodone may be offered.
   * If the initial opioid dose is insufficient for pain relief, an additional 5 mg oxycodone may be offered upto a maximum of 10 mg (total dose).
   If a subject is unable to tolerate PO medication (or the PO oxycodone pain relief is insufficient), IV morphine (initiated at 2 mg) or hydromorphone (initiated at 0.2 my) may be administered.
10. Document all AEs with an onset after the subject is randomized and SAEs with an onset the subject signs the ICF.

*FIG. 5 (Cont.2)*

Table 3   Area Under the Curve of Numeric Rating Scale Pain Intensity Score at 0-96 h Post-surgery – Worst Observation Carried Forward Within the Therapeutic of Opioid; Multiple Imputation Method (Efficacy Analysis Set)

| | EXP133-ADMIX (N = 85) | BUP50 (N = 81) | 95% CI | p-value[1] | % Reduct in LSM[2] |
|---|---|---|---|---|---|
| AUC of NRS Pain Intensity Score; n[3] | 85 | 81 | | | |
| Mean (SD) | 594.44 (191.650) | 650.05 (178.952) | | | |
| Median (Min, max) | 612.64 (129.2, 958.1) | 676.92 (207.7, 943.7) | | | |
| LSM (SE)[4] | 568.9 (20.07) | 634.7 (20.04) | | | |
| LSM difference from bupivacaine (SE)[4] | −65.8 (26.97) | | −118.7, −12.9 | 0.0074 | 10.37 |

Abbreviations: ANCOVA = analysis of covariance; AUC = area under the curve; $H_a$ = alternative hypothesis; LSM = least squares mean; Max = maximum; Min = minimum; NRS = Numeric Rating Scale; Reduct = reduction; SE = standard error; SD = standard deviation. NRS = 0 (no pain), 1, 2, ..., 9, and 10 (worst possible pain). Duplicate scores were removed and the worst score was retained if it was collected with the same date/time of another score.

1. 1-sided p-value for LSM difference. 1-sided test for $H_a$: Mean AUC for EXPAREL admix < mean AUC for bupivacaine HCl.
2. Percent reduction was calculated as (LSM for bupivacaine HCl − LSM for EXPAREL admix)/LSM for bupivacaine × 100%.
3. Area under the pain-time curve was calculated using the trapezoidal method for the imputed data.
4. From an ANCOVA with mean effect of treatment, categorical covariate of pooled investigator site, and continuous covariates of age and height.

*FIG. 6*

Table 4  Area Under the Curve of Numeric Rating Scale Pain Intensity Score by Time Interval – Worst Observation Carried Forward Within the Therapeutic of Opioid; Multiple Imputation Method (Efficacy Analysis Set)

| AUC of NRS Pain Intensity Score | EXP133-ADMIX (N = 85) | BUP50 (N = 81) | 95% CI | p-value[1] | % Reduct in LSM[2] |
|---|---|---|---|---|---|
| At 0-24 h post-surgery; n | 85 | 81 | | | |
| Mean (SD)[3] | 158.52 (42.500) | 165.93 (43.200) | | | |
| Median (Min, max) | 155.78 (52.9, 238.5) | 175.98 (71.4, 226.3) | | | |
| LSM (SE)[4] | 155.6 (4.73) | 165.6 (4.72) | | | |
| LSM difference from bupivacaine (SE)[4] | -10.0 (6.35) | | -22.4, 2.5 | 0.0578 | 6.04 |
| At 0-48 h post-surgery; n | 85 | 81 | | | |
| Mean (SD)[3] | 327.23 (87.256) | 351.23 (75.932) | | | |
| Median (Min, max) | 342.38 (110.2, 478.1) | 376.55 (158.4, 466.3) | | | |
| LSM (SE)[4] | 317.9 (9.04) | 348.1 (9.02) | | | |
| LSM difference from bupivacaine (SE)[4] | -30.2 (12.14) | | -53.9, -6.4 | 0.0065 | 8.68 |
| At 0-72 h post-surgery; n | 85 | 81 | | | |
| Mean (SD)[3] | 461.98 (138.913) | 503.90 (124.950) | | | |
| Median (Min, max) | 463.73 (129.2, 718.1) | 528.79 (188.4, 703.7) | | | |
| LSM (SE)[4] | 445.2 (14.39) | 494.7 (14.36) | | | |
| LSM difference from bupivacaine (SE)[4] | -49.4 (19.33) | | -87.3, -11.6 | 0.0053 | 10.01 |
| At 24-48 h post-surgery; n | 85 | 81 | | | |
| Mean (SD)[3] | 168.71 (50.354) | 185.30 (42.037) | | | |
| Median (Min, max) | 173.58 (49.0, 240.0) | 189.40 (81.4, 240.0) | | | |
| LSM (SE)[4] | 162.3 (5.16) | 182.5 (5.15) | | | |
| LSM difference from bupivacaine (SE)[4] | -20.2 (6.93) | | -33.8, -6.6 | 0.0018 | 11.07 |

FIG. 7

Abbreviations: ANCOVA = analysis of covariance; AUC = area under the curve; $H_a$ = alternative hypothesis; Max = maximum; Min = minimum; LSM = least squares mean; NRS = Numeric Rating Scale; Reduct = reduction; SE = standard error; SD = standard deviation.

NRS = 0 (no pain), 1, 2, ..., 9, and 10 (worst possible pain). Duplicate scores were removed and the worst score was retained if it was collected with the same date/time of another score.

1. 1-sided p-value for LSM difference. One-sided test for $H_a$ = mean AUC for EXPAREL admix < mean AUC for bupivacaine HCl.
2. Percent reduction was calculated as (LSM for bupivacaine − LSM for EXPAREL admix)/LSM for bupivacaine × 100%.
3. Area under the pain-time curve was calculated using the trapezoidal method for the imputed data.
4. From an ANCOVA with mean effect of treatment, categorical covariate of pooled investigator site, and continuous covariates of age and height.

Table 4 (con't) Area Under the Curve of Numeric Rating Scale Pain Intensity Score by Time Interval – Worst Observation Carried Forward Within the Therapeutic of Opioid; Multiple Imputation Method (Efficacy Analysis Set)

| AUC of NRS Pain Intensity Score | EXP133-ADMIX (N = 85) | BUP50 (N = 81) | 95% CI | p-value1 | % Reduct in LSM2 |
|---|---|---|---|---|---|
| At 24-72 h post-surgery; n | 85 | 81 | | | |
| Mean (SD)3 | 303.46 (105.310) | 337.97 (94.599) | | | |
| Median (Min, max) | 307.95 (54.4, 480.0) | 346.34 (111.4, 480.0) | | | |
| LSM (SE)4 | 289.7 (10.86) | 329.1 (10.84) | | | |
| LSM difference from bupivacaine (SE)4 | −39.5 (14.59) | | −68.1, −10.8 | 0.0034 | 11.97 |
| At 24-96 h post-surgery; n | 85 | 81 | | | |
| Mean (SD)3 | 435.92 (160.327) | 484.12 (150.785) | | | |
| Median (Min, max) | 436.60 (54.4, 720.0) | 500.95 (130.7, 720.0) | | | |
| LSM (SE)4 | 413.3 (16.83) | 469.1 (16.80) | | | |
| LSM difference from bupivacaine (SE)4 | −55.8 (22.61) | | −100.1, −11.5 | 0.0068 | 11.90 |

FIG. 7 (Cont.1)

| | | | | |
|---|---|---|---|---|
| At 48-72 h post-surgery; n | 85 | 81 | | |
| Mean (SD)[3] | 134.75 (62.928) | 152.66 (57.737) | | |
| Median (Min, max) | 133.69 (0.0, 240.0) | 155.02 (25.2, 240.0) | | |
| LSM (SE)[4] | 127.3 (6.51) | 146.6 (6.50) | | |
| LSM difference from bupivacaine (SE)[4] | -19.3 (8.75) | | -36.4, -2.1 | 0.0138 | 13.17 |
| At 48-96 h post-surgery; n | 85 | 81 | | |
| Mean (SD)[3] | 267.21 (120.519) | 298.82 (116.190) | | |
| Median (Min, max) | 256.50 (0.0, 480.0) | 302.93 (36.8, 480.0) | | |
| LSM (SE)[4] | 251.0 (12.80) | 286.6 (12.78) | | |
| LSM difference from bupivacaine (SE)[4] | -35.6 (17.20) | | -69.3, -1.9 | 0.0191 | 12.42 |
| At 72-96 h post-surgery; n | 85 | 81 | | |
| Mean (SD)[3] | 132.46 (63.289) | 146.16 (63.683) | | |
| Median (Min, max) | 132.14 (0.0, 240.0) | 154.29 (11.6, 240.0) | | |
| LSM (SE)[4] | 123.7 (6.97) | 140.0 (6.95) | | |
| LSM difference from bupivacaine (SE)[4] | -16.3 (9.36) | | -34.7, 2.0 | 0.0404 | 11.64 |

Abbreviations: ANCOVA = analysis of covariance; AUC = area under the curve; $H_a$ = alternative hypothesis; Max = maximum; Min = minimum; LSM = least squares mean; NRS = Numeric Rating Scale; Reduct = reduction; SE = standard error; SD = standard deviation.

NRS = 0 (no pain), 1, 2, ..., 9, and 10 (worst possible pain). Duplicate scores were removed and the worst score was retained if it was collected with the same date/time of another score.

1. 1-sided p-value for LSM difference. One-sided test for $H_a$ = mean AUC for EXPAREL admix < mean AUC for bupivacaine HCl.
2. Percent reduction was calculated as (LSM for bupivacaine − LSM for EXPAREL admix)/LSM for bupivacaine × 100%.
3. Area under the pain-time curve was calculated using the trapezoidal method for the imputed data.
4. From an ANCOVA with mean effect of treatment, categorical covariate of pooled investigator site, and continuous covariates of age and height.

FIG. 7 (Cont.2)

Table 5  Analysis and Summary of Total Opioid Consumption by Time Interval (Efficacy Analysis Set)

| Total Opioid Consumption (OMED) | EXP133-ADMIX (N = 85) | BUP50 (N = 81) | p-value[1] | p-value[2] | % Reduction in LSM[3] |
|---|---|---|---|---|---|
| At 0-24 h post-surgery; n | 85 | 81 | | | |
| Geometric mean | 38.76 | 50.29 | | | |
| % Coefficient of variation | 48.959 | 47.632 | | | |
| Median (Min, max) | 43.50 (0.0, 109.5) | 57.50 (7.5, 135.5) | | | |
| LSM (95% CI)[4] | 37.54 (32.68, 43.12) | 48.92 (42.59, 56.17) | 0.0027 | 0.0040 | 23.26 |
| LSM ratio over bupivacaine (95% CI) | 0.77 (0.64, 0.92) | | | | |
| At 0-48 h post-surgery; n | 85 | 81 | | | |
| Geometric mean | 70.04 | 90.09 | | | |
| % Coefficient of variation | 49.362 | 44.999 | | | |
| Median (Min, max) | 79.50 (7.5, 195.5) | 103.50 (22.5, 256.5) | | | |
| LSM (95% CI)[4] | 67.02 (59.21, 75.85) | 88.66 (78.35, 100.33) | 0.0005 | 0.0029 | 24.41 |
| LSM ratio over bupivacaine (95% CI) | 0.76 (0.64, 0.89) | | | | |
| At 0-72 h post-surgery; n | 85 | 81 | | | |
| Geometric mean | 90.62 | 114.08 | | | |
| % Coefficient of variation | 52.882 | 47.228 | | | |
| Median (Min, max) | 102.00 (7.5, 270.5) | 133.50 (22.5, 326.0) | | | |
| LSM (95% CI)[4] | 85.38 (75.14, 97.02) | 111.35 (98.02, 126.50) | 0.0012 | 0.0058 | 23.32 |
| LSM ratio over bupivacaine (95% CI) | 0.77 (0.65, 0.91) | | | | |

Abbreviations: ANCOVA = analysis of covariance; CI = confidence interval; H$_a$ = alternative hypothesis; LSM = least squares mean; Max = maximum; Min = minimum; OMED = oral morphine equivalent.

1. 1-sided p-value for LSM difference. One-sided test for H$_a$ = mean total opioid consumption for EXPAREL admix < mean total opioid consumption for bupivacaine HCl.
2. 2-sided p-value for Cochran-Mantel-Haenszel test. Two-sided Cochran-Mantel-Haenszel test for the row mean score difference was calculated using modified ridit scores stratified by pooled investigator site.
3. Percent reduction was calculated as (LSM for EXPAREL admix)/LSM for bupivacaine × 100%.
4. From an ANCOVA with main effect of treatment and covariates of site (categorical) and age (continuous). Total dose is log-transformed in the analysis and back transformed in the presentation. Zero (0) dose is replaced with 3.75 mg to enable log-transformation for 0-96 h time interval.

FIG. 8

Table 5  Analysis and Summary of Total Opioid Consumption by Time Interval (Efficacy Analysis Set)

| Total Opioid Consumption (OMED) | EXP133-ADMIX (N = 85) | BUP50 (N = 81) | p-value[1] | p-value[2] | % Reduction in LSM[3] |
|---|---|---|---|---|---|
| % Coefficient of variation | 54.420 | 48.284 | | | |
| Median (Min, max) | 125.50 (7.5, 355.5) | 159.00 (22.5, 387.0) | | | |
| LSM (95% CI) | 101.81 (89.12, 116.31) | 132.84 (116.31, 151.72) | | | |
| LSM ratio over bupivacaine (95% CI)[4] | 0.77 (0.64, 0.92) | | 0.0018 | 0.0071 | 23.36 |
| At 24-48 h post-surgery, n | 85 | 81 | | | |
| Geometric mean | 27.96 | 37.02 | | | |
| % Coefficient of variation | 60.275 | 54.255 | | | |
| Median (Min, max) | 34.50 (0.0, 92.0) | 37.50 (7.5, 121.0) | | | |
| LSM (95% CI)[4] | 25.86 (21.93, 30.51) | 36.00 (30.53, 42.45) | | | |
| LSM ratio over bupivacaine (95% CI) | 0.72 (0.58, 0.90) | | 0.0017 | 0.0201 | 28.17 |
| At 24-72 h post-surgery, n | 85 | 81 | | | |
| Geometric mean | 47.73 | 59.44 | | | |
| % Coefficient of variation | 63.949 | 57.146 | | | |
| Median (Min, max) | 60.00 (0.0, 187.5) | 67.50 (7.5, 211.5) | | | |
| LSM (95% CI)[4] | 43.16 (36.65, 50.83) | 56.60 (48.08, 66.64) | | | |
| LSM ratio over bupivacaine (95% CI) | 0.76 (0.61, 0.95) | | 0.0078 | 0.0259 | 23.75 |
| At 24-96 h post-surgery, n | 85 | 81 | | | |
| Geometric mean | 65.29 | 80.62 | | | |
| % Coefficient of variation | 64.897 | 57.652 | | | |
| Median (Min, max) | 76.00 (0.0, 277.5) | 97.50 (7.5, 267.0) | | | |
| LSM (95% CI)[4] | 58.39 (49.25, 69.22) | 75.99 (64.11, 90.06) | | | |
| LSM ratio over bupivacaine (95% CI) | 0.77 (0.61, 0.97) | | 0.0120 | 0.0217 | 23.16 |

Abbreviations: ANCOVA = analysis of covariance; CI = confidence interval; $H_a$ = alternative hypothesis; LSM = least squares mean; Max = maximum; Min = minimum; OMED = oral morphine equivalent.

1. 1-sided p-value for LSM difference. One-sided test for $H_a$ = mean total opioid consumption for EXPAREL admix < mean total opioid consumption for bupivacaine HCl.
2. 2-sided p-value for Cochran-Mantel-Haenszel test. Two-sided Cochran-Mantel-Haenszel test for the row mean score difference was calculated using modified ridit scores stratified by pooled investigator site.
3. Percent reduction was calculated as (LSM for EXPAREL admix)/LSM for bupivacaine × 100%.
4. From an ANCOVA with main effect of treatment and covariates of site (categorical) and age (continuous). Total dose is log-transformed in the analysis and back transformed in the presentation. Zero (0) dose is replaced with 3.75 mg to enable log-transformation for 0-96 h time interval.

FIG. 8 (Cont.1)

Table 5  Analysis and Summary of Total Opioid Consumption by Time Interval (Efficacy Analysis Set)

| Total Opioid Consumption (OMED) | EXP133-ADMIX (N = 85) | BUP50 (N = 81) | p-value[1] | p-value[2] | % Reduction in LSM[3] |
|---|---|---|---|---|---|
| % Coefficient of variation | 80.749 | 71.807 | | | |
| Median (Min, max) | 22.50 (0.0, 96.0) | 30.00 (0.0, 94.5) | | | |
| LSM (95% CI)[4] | 12.76 (9.81, 16.59) | 17.27 (13.29, 22.44) | 0.0463 | 0.1818 | 26.11 |
| LSM ratio over bupivacaine (95% CI) | 0.74 (0.52, 1.05) | | | | |
| At 48-96 h post-surgery, n | 85 | 81 | | | |
| Geometric mean | 31.00 | 38.49 | | | |
| % Coefficient of variation | 76.918 | 73.387 | | | |
| Median (Min, max) | 45.00 (0.0, 186.0) | 52.50 (0.0, 222.5) | | | |
| LSM (95% CI)[4] | 26.14 (20.46, 33.39) | 34.77 (27.23, 44.41) | 0.0446 | 0.1442 | 24.82 |
| LSM ratio over bupivacaine (95% CI) | 0.75 (0.54, 1.04) | | | | |
| At 72-96 h post-surgery, n | 85 | 81 | | | |
| Geometric mean | 13.12 | 15.23 | | | |
| % Coefficient of variation | 82.141 | 105.215 | | | |
| Median (Min, max) | 22.50 (0.0, 90.0) | 22.50 (0.0, 215.0) | | | |
| LSM (95% CI)[4] | 11.17 (8.26, 15.10) | 13.52 (10.00, 18.27) | 0.1780 | 0.2030 | 17.38 |
| LSM ratio over bupivacaine (95% CI) | 0.83 (0.55, 1.24) | | | | |

Abbreviations: ANCOVA = analysis of covariance; CI = confidence interval; $H_a$ = alternative hypothesis; LSM = least squares mean; Max = maximum; Min = minimum; OMED = oral morphine equivalent.

1. 1-sided p-value for LSM difference. One-sided test for $H_a$ = mean total opioid consumption for EXPAREL admix < mean total opioid consumption for bupivacaine HCl.
2. 2-sided p-value for Cochran-Mantel-Haenszel test. Two-sided Cochran-Mantel-Haenszel test for the row mean score difference was calculated using modified ridit scores stratified by pooled investigator site.
3. Percent reduction was calculated as (LSM for bupivacaine – LSM for EXPAREL admix)/LSM for bupivacaine × 100%.
4. From an ANCOVA with main effect of treatment and covariates of site (categorical) and age (continuous). Total dose is log-transformed in the analysis and back transformed in the presentation. Zero (0) dose is replaced with 3.75 mg to enable log-transformation for 0-96 h time interval.

FIG. 8 (Cont. 2)

Table 6  Summary of Time to First Opioid Consumption Post-surgery (Efficacy Analysis Set)

| | EXP133-ADMIX (N = 85) | BUP50 (N = 81) |
|---|---|---|
| Subjects taking opioid rescue medication, n (%) | 85 (100.0) | 81 (100.0) |
| Time (h) to first rescue medication[1] | | |
| 25th percentile (95% CI) | 2.67 (1.78, 3.47) | 2.50 (1.95, 2.87) |
| Median (95% CI) | 4.15 (3.80, 4.83) | 3.63 (2.98, 4.05) |
| 75th percentile (95% CI) | 6.13 (5.12, 7.33) | 4.80 (4.20, 5.07) |
| Minimum, maximum | 0.0, 25.1 | 0.2, 15.9 |
| Comparison to bupivacaine | | |
| Hazard Ratio (95% CI) from Cox Model[2] | 0.70 (0.51, 0.96) | |
| 1-sided p-value from Cox Model | 0.0127 | |
| 2-sided p-value from Log-rank Test[3] | 0.0578 | |

Abbreviations: CI = confidence interval.
Mean observation was censored.

1. Kaplan-Meier estimate.
2. Cox proportional hazards model with treatment as main effect, pooled Investigator site as categorical covariate, and age and height as continuous covariates. P-value was from the F-test for the between-treatment comparison in the Cox model.
3. Log-rank test stratified by pooled Investigator site.

FIG. 9

Table 7  Summary of the Worst and Average Numeric Rating Scale Pain Intensity Scores Over the Last 24 h From Post-surgery Day 1 Through Day 14 (Efficacy Analysis Set)

| Post-surgery Day | Worst Pain | | | | Average Pain | | | |
|---|---|---|---|---|---|---|---|---|
| | EXP133-ADMIX (N = 85) | BUP50 (N = 81) | LSM Diff | p-value[2] | EXP133-ADMIX (N = 85) | BUP50 (N = 81) | LSM Diff | p-value[2] |
| Day 1; n | 85 | 81 | | | 85 | 81 | | |
| Mean (SD) | 8.6 (1.63) | 8.7 (1.77) | | | 6.7 (1.89) | 6.6 (2.00) | | |
| Median (Min, max) | 9.0 (4, 10) | 10.0 (4, 10) | | | 7.0 (1, 10) | 7.0 (2, 10) | | |
| LSM (SE)[3] | 8.6 (0.20) | 8.7 (0.19) | -0.1 (0.26) | 0.3674 | 6.4 (0.22) | 6.5 (0.22) | -0.1 (0.29) | 0.3606 |
| 95% CI | 8.2, 9.0 | 8.3, 9.1 | -0.6, 0.4 | | 6.0, 6.9 | 6.1, 7.0 | -0.7, 0.5 | |
| Day 2; n | 85 | 78 | | | 85 | 78 | | |
| Mean (SD) | 7.9 (1.98) | 8.2 (1.81) | | | 5.8 (2.03) | 6.2 (1.84) | | |
| Median (Min, max) | 8.0 (2, 10) | 8.0 (4, 10) | | | 6.0 (0, 10) | 7.0 (2, 10) | | |
| LSM (SE)[3] | 7.7 (0.21) | 8.1 (0.21) | -0.4 (0.29) | 0.1016 | 5.5 (0.21) | 6.1 (0.21) | -0.6 (0.28) | 0.0184 |
| 95% CI | 7.3, 8.1 | 7.7, 8.5 | -0.9, 0.2 | | 5.1, 5.9 | 5.7, 6.5 | -1.1, -0.0 | |
| Day 3; n | 84 | 78 | | | 84 | 78 | | |
| Mean (SD) | 6.8 (2.33) | 7.5 (2.14) | | | 5.2 (2.14) | 5.7 (2.08) | | |
| Median (Min, max) | 7.0 (1, 10) | 8.0 (3, 10) | | | 5.0 (1, 10) | 6.0 (2, 10) | | |
| LSM (SE)[3] | 6.7 (0.25) | 7.4 (0.25) | -0.7 (0.34) | 0.0215 | 5.0 (0.23) | 5.5 (0.23) | -0.5 (0.31) | 0.0476 |
| 95% CI | 6.2, 7.2 | 6.9, 7.9 | -1.4, -0.0 | | 4.5, 5.4 | 5.0, 5.9 | -1.1, 0.1 | |
| Day 4; n | 85 | 78 | | | 85 | 78 | | |
| Mean (SD) | 6.6 (2.24) | 7.0 (2.34) | | | 4.8 (2.18) | 5.2 (1.96) | | |
| Median (Min, max) | 7.0 (1, 10) | 8.0 (2, 10) | | | 5.0 (1, 10) | 6.0 (1, 9) | | |
| LSM (SE)[3] | 6.4 (0.25) | 6.9 (0.26) | -0.5 (0.34) | 0.0794 | 4.6 (0.22) | 5.1 (0.23) | -0.5 (0.31) | 0.0529 |
| 95% CI | 5.9, 6.9 | 6.4, 7.4 | -1.2, 0.2 | | 4.1, 5.0 | 4.6, 5.5 | -1.1, 0.1 | |

Abbreviations: ANCOVA = analysis of covariance; CI = confidence interval; Diff = difference; $H_a$ = alternative hypothesis; LSM = least squares mean; Max = maximum; Min = minimum; SD = standard deviation; SE = standard error.
1. Difference from bupivacaine.
2. 1-sided p-value for LSM difference. One-sided test for $H_a$ = mean pain intensity score for EXPAREL admix < mean pain intensity score for bupivacaine.
3. From ANCOVA with main effect of treatment, categorical covariate of pooled Investigator site, and continuous covariates of age and height.

FIG. 10

Table 8 Summary of Pharmacokinetic Parameters (PK Parameter Analysis Set)

| | EXP133-ADMIX (N = 24) | BUP50 (N = 18) |
|---|---|---|
| $AUC_{0-last}$ (h × ng/mL); n | 24 | 18 |
| Geometric mean (%CV) | 23064.09 (47.6) | 6571.35 (47.4) |
| Mean (SD) | 25038.63 (11921.063) | 7283.31 (3453.896) |
| Median (Min, max) | 23176.53 (13076.2, 62763.2) | 6461.32 (2619.2, 14797.0) |
| $AUC_{0-\infty}$ (h × ng/mL); n | 24 | 18 |
| Geometric Mean (%CV) | 23137.28 (47.5) | 6707.51 (47.1) |
| Mean (SD) | 25109.09 (11917.662) | 7446.40 (3510.207) |
| Median (Min, max) | 23237.77 (13147.4, 62780.2) | 6484.24 (2645.0, 14836.7) |
| $AUC_{extr}$ (%); n | 24 | 18 |
| Geometric Mean (%CV) | 0.21 (106.1) | 0.60 (263.9) |
| Mean (SD) | 0.32 (0.335) | 1.89 (4.995) |
| Median (Min, max) | 0.19 (0.0, 1.5) | 0.40 (0.1, 21.6) |
| $C_{max}$ (ng/mL); n | NA | 18 |
| Geometric mean (%CV) | NA | 307.75 (44.4) |
| Mean (SD) | NA | 333.89 (148.217) |
| Median (Min, max) | NA | 283.00 (147.0, 735.0) |
| Early $C_{max}$ (ng/mL); n | 24 | NA |
| Geometric mean (%CV) | 419.60 (41.4) | NA |
| Mean (SD) | 467.04 (193.163) | NA |
| Median (Min, max) | 491.50 (117.0, 846.0) | NA |
| Late $C_{max}$ (ng/mL); n | 24 | NA |
| Geometric mean (%CV) | 313.93 (40.2) | NA |
| Mean (SD) | 334.79 (134.517) | NA |
| Median (Min, max) | 303.00 (161.0, 766.0) | NA |

Abbreviations: AUC; $AUC_{0-\infty}$ = area under the curve from the time of dosing to infinity; $AUC_{0-last}$ = area under the curve from the time of dosing to the last quantifiable concentration; $AUC_{extr}$ = extrapolated area under the curve from time of last point above lower limit of quantification to infinity; CL/F = apparent clearance; $C_{max}$ = maximum plasma concentration; CV = coefficient of variation; max = maximum; Min = minimum; NA = not applicable; PK = pharmacokinetic; SD = standard deviation; $t_{1/2el}$ = apparent terminal elimination half-life; $T_{max}$ = time of maximum plasma concentration; $V_d/F$ = apparent volume of distribution.

FIG. 13

Table 8  Summary of Pharmacokinetic Parameters (PK Parameter Analysis Set)

| | EXP133-ADMIX (N = 24) | BUP50 (N = 18) |
|---|---|---|
| $T_{max}$ (h); n | NA | 18 |
| Median (Min, max) | NA | 0.65 (0.5, 30.8) |
| Early $T_{max}$ (h); n | 24 | NA |
| Median (Min, max) | 0.63 (0.4, 1.2) | NA |
| Late $T_{max}$ (h); n | 24 | NA |
| Median (Min, max) | 60.94 (8.2, 82.4) | NA |
| $t_{1/2el}$ (h) | | |
| Geometric mean (%CV) | 11.15 (24.9) | 9.56 (40.0) |
| Mean (SD) | 11.43 (2.844) | 10.19 (4.074) |
| Median (Min, max) | 10.63 (7.9, 21.2) | 9.17 (5.0, 20.4) |
| CL/F (L/h) | 24 | 18 |
| Geometric mean (%CV) | 9.10 (35.0) | 11.57 (50.3) |
| Mean (SD) | 9.73 (3.403) | 12.90 (6.486) |
| Median (Min, max) | 9.06 (3.4, 16.0) | 12.00 (5.2, 29.3) |
| $V_d/F$ (L) | 24 | 18 |
| Geometric mean (%CV) | 146.41 (43.4) | 159.59 (52.5) |
| Mean (SD) | 162.38 (70.460) | 181.43 (95.238) |
| Median (Min, max) | 152.48 (38.1, 356.7) | 168.37 (80.7, 397.5) |

Abbreviations: $AUC_{0-\infty}$ = area under the curve from the time of dosing to infinity; $AUC_{0-last}$ = area under the curve from the time of dosing to the last quantifiable concentration; $AUC_{extr}$ = extrapolated area under the curve from time of last point above lower limit of quantification to infinity; CL/F = apparent clearance; $C_{max}$ = maximum plasma concentration; CV = coefficient of variation; max = maximum; Min = minimum; NA = not applicable; PK = pharmacokinetic; SD = standard deviation; $t_{1/2el}$ = apparent terminal elimination half-life; $T_{max}$ = time of maximum plasma concentration; $V_d/F$ = apparent volume of distribution.

FIG. 13 (Cont.)

Table 9  Summary of Time to Onset and Duration of Motor and Sensory Block (PD Analysis Set)

| | EXP133-ADMIX (N = 24) | BUP50 (N = 21) |
|---|---|---|
| Number of subjects with motor block, n (%) | | |
| Onset observed | 1 (4.2) | 0 |
| Onset censored | 23 (95.8) | 21 (100.0) |
| Time (h) to onset of motor block[1] | | |
| 25th percentile (95% CI) | NE (0.88, NE) | NE (NE, NE) |
| Median (95% CI) | NE (0.88, NE) | NE (NE, NE) |
| 75th percentile (95% CI) | NE (NE, NE) | NE (NE, NE) |
| Minimum, maximum | $0.2^2$, $1.0^2$ | $0.2^2$, $1.0^2$ |
| Duration (h) of motor block[1] | | |
| 25th percentile (95% CI) | NE (71.05, NE) | NE (NE, NE) |
| Median (95% CI) | NE (71.5, NE) | NE (NE, NE) |
| 75th percentile (95% CI) | NE (NE, NE) | NE (NE, NE) |
| Minimum, maximum | $1.3^2$, $166.3^2$ | $6.0^2$, $117.9^2$ |
| Ratio over bupivacaine | NE | |
| Comparison to bupivacaine in duration of motor block | | |
| 2-sided p-value from log-rank test[3] | NE | NE |
| Cox proportional hazards model (95% CI)[4] | NE | NE |
| 1-sided p-value from Cox model | NE | NE |
| Number of subjects with sensory block, n (%) | | |
| Onset observed | 15 (62.5) | 13 (61.9) |
| Onset censored | 9 (37.5) | 8 (38.1) |
| Time (h) to onset of sensory block[1] | | |
| 25th percentile (95% CI) | 0.42 (0.23, 0.52) | 0.28 (0.22, 0.43) |
| Median (95% CI) | 0.53 (0.42, 0.68) | 0.43 (0.28, 0.83) |
| 75th percentile (95% CI) | 0.68 (0.53, NE) | 0.83 (0.43, NE) |

FIG. 14

| | 0.22, 1.0 | 0.22, 1.0 |
|---|---|---|
| Minimum, maximum | | |
| Duration (h) of sensory block[1] | | |
| 25th percentile (95% CI) | 6.97 (1.75, 11.60) | 7.17 (1.98, 11.63) |
| Median (95% CI) | 22.90 (6.97, 94.37) | 11.63 (7.15, 23.25) |
| 75th percentile (95% CI) | 94.37 (22.90, NE) | 23.25 (11.63, NE) |
| Minimum, maximum | 1.12, 143.6 | 1.32, 23.8 |
| Ratio over bupivacaine | 1.968 | |
| Comparison to bupivacaine in duration of sensory block | | |
| 2-sided p-value from log-rank test[3] | 0.2364 | |
| Cox proportional hazards model (95% CI)[4] | 0.61 (0.26, 1.41) | |
| 1-sided p-value from Cox model | 0.1222 | |

Table 9

Abbreviations: CI = confidence interval; NE = not estimatable; PD = pharmacodynamic.

Time to onset of motor block was defined as time from the end of study drug administration to the earliest time of no knee extension. If no onset of motor block was obtained, time was censored at the last onset assessment time prior to surgery.

Time to onset of sensory block was defined as time from the end of study drug administration to the earliest time of no light touch sensation in both proximal and distal locations. If no onset of sensory block was obtained, time was censored at the last onset assessment time prior to surgery.

Duration of motor block was defined as the time from motor block onset to the earliest time of normal knee extension. If no normal motor movement was obtained, duration was calculated as the time from the motor block onset to the last assessment time and considered as censored for the Kaplan-Meier estimate.

Duration of sensory block was defined as the time from sensory block onset to the earliest time of normal light touch sensation at both proximal and distal locations. If no normal sensation was obtained, duration was calculated as the time from the sensory block onset to the last assessment time and considered as censored for the Kaplan-Meier estimate.

1. Kaplan-Meier estimate.
2. Observation was censored.
3. Log-rank test stratified by pooled Investigator site.
4. Cox proportional hazards model with treatment as main effect, pooled Investigator site as categorical covariate, and age and height as continuous covariates. P-value was from the F-test for the between-treatment comparison in the Cox model.

FIG. 14 (Cont. 1)

Table 10 Overview of Treatment-emergent Adverse Events (Safety Analysis Set)

| | EXP133-ADMIX (N = 86) n (%) | BUP50 (N = 80) n (%) | Total (N = 166) n (%) |
|---|---|---|---|
| Subjects with any TEAE | 77 (89.5) | 71 (88.8) | 148 (89.2) |
| Maximum severity of mild | 51 (59.3) | 51 (63.8) | 102 (61.4) |
| Maximum severity of moderate Maximum severity | 24 (27.9) | 19 (23.8) | 43 (25.9) |
| | 2 (2.3) | 1 (1.3) | 3 (1.8) |
| Subjects with ≥1 related TEAE Subjects | 3 (3.5) | 2 (2.5) | 5 (3.0) |
| with ≥1 SAE | 3 (3.5) | 3 (3.8) | 6 (3.6) |
| Subjects with ≥1 AESI | 3 (3.5) | 1 (1.3) | 4 (2.4) |
| Subjects that discontinued due to a TEAE | 0 | 0 | 0 |
| Deaths during the study | 0 | 0 | 0 |

Abbreviations: AESI = adverse event of special interest; TEAE = treatment-emergent adverse event; SAE = serious adverse event.

FIG. 15

Table 11 Summary of Treatment-emergent Adverse Events Occuring in ≥5% of Subjects in Any Cohort (Safety Analysis Set)

| System Organ Class<br>Preferred Term | EXP133-ADM IX<br>(N = 86)<br>n (%) | BUP50<br>(N = 80)<br>n (%) | Total<br>(N = 166)<br>n (%) |
|---|---|---|---|
| Subjects with ≥1 TEAE | 77 (89.5) | 71 (88.8) | 148 (89.2) |
| Gastrointestinal disorders | 57 (66.3) | 49 (61.3) | 106 (63.9) |
| Nausea | 34 (39.5) | 30 (37.5) | 64 (38.6) |
| Constipation | 30 (34.9) | 31 (38.8) | 61 (36.7) |
| Vomiting | 5 (5.8) | 6 (7.5) | 11 (6.6) |
| Musculoskeletal and connective tissue disorders | 14 (16.3) | 13 (16.3) | 27 (16.3) |
| Muscle spasms | 11 (12.8) | 9 (11.3) | 20 (12.0) |
| Psychiatric disorders | | | |
| Insomnia | 10 (11.6) | 16 (20.0) | 26 (15.7) |
| Nervous system disorders | | | |
| Headache | 5 (5.8) | 13 (16.3) | 18 (10.8) |
| Vascular disorders | 20 (23.3) | 3 (3.8) | 23 (13.9) |
| Hypotension | 13 (15.1) | 2 (2.5) | 15 (9.0) |
| Hypertension | 10 (11.6) | 13 (16.3) | 23 (13.9) |
| Skin and subcutaneous tissue disorders | 3 (3.5) | 8 (10.0) | 11 (6.6) |
| Pruritus | 5 (5.8) | 4 (5.0) | 9 (5.4) |
| Cardiac disorders | 8 (9.3) | 8 (10.0) | 16 (9.6) |
| | 6 (7.0) | 4 (5.0) | 10 (6.0) |
| | 6 (7.0) | 9 (11.3) | 15 (9.0) |
| Tachycardia | 4 (4.7) | 5 (6.3) | 9 (5.4) |

Abbreviations: MedDRA = Medical Dictionary for Regulatory Activities; TEAE = treatment-emergent adverse event.
Adverse events were coded using MedDRA version 24.1.
Subjects that experienced the same TEAE more than once were counted only once at each summary level.

FIG. 16

TREATMENT OF PAIN ASSOCIATED WITH TOTAL KNEE ARTHROPLASTY WITH SUSTAINED-RELEASE LIPOSOMAL ANESTHETIC COMPOSITIONS

CROSS-REFERENCE TO RELATED APPLICATIONS

This application claims the benefit of U.S. Provisional Application No. 63/422,146, filed Nov. 3, 2022, which is incorporated by reference herein in its entirety.

BACKGROUND

Postsurgical pain is one of the most common forms of acute pain, which is the normal physiological response to tissue insult or injury and has adaptive value by serving as a warning of danger or damage. Most acute pain is either treatable or avoidable, especially when it occurs in a clinical setting. However, if acute pain is poorly or inappropriately treated, it may progress to chronic pain. Thus, effective postsurgical pain control is a critical element in patient recovery following surgery, as the majority of patients may experience significant pain, particularly in the first few days. Improved postsurgical pain management contributes to better healing, faster patient mobilization, shortened hospital stays, and reduced healthcare costs.

Knee surgery, including knee arthroplasty, is usually used to manage pain and disability in the knee. However, total knee arthroplasty (TKA) is recognized as a painful orthopedic procedure, wherein over half of those undergoing TKA experience severe postoperative pain. Opioids are commonly used to manage post-operative orthopedic pain. Opioid use carries a risk of developing tolerance and dependence. Thus, an important goal following surgery is to improve analgesia while reducing opioid consumption.

Multimodal pain management approaches are recommended by professional societies to improve analgesia, reduce opioid use, and decrease opioid-related adverse events (AEs) following knee surgery. It is recommended that protocols include long-acting neuraxial opioids together with scheduled acetaminophen and nonsteroidal anti-inflammatory drugs (NSAIDs). However, most many orthopedic pain patients still request opioids after cesarean delivery for breakthrough pain. Thus, there continues to be a need for methods of treating pain associated with surgery, including knee surgery in a subject.

SUMMARY

Provided herein are methods of administering to the adductor canal of a patient a pharmaceutical composition for post-operative analgesia, comprising: (a) selecting an entry point of an injection needle in a leg of a patient by ultrasound transducer; (b) inserting the injection needle into the patient at the entry point; (c) identifying a first nerve in the leg of the patient; (d) administering to the first nerve saline and a pharmaceutical composition; (e) identifying a second nerve in the leg of the patient; (f) administering to the second nerve saline and the pharmaceutical composition; wherein the first nerve and second nerve are selected from the group consisting of the nerve to vastus medialis (NVM) and the saphenous nerve, and wherein the first nerve is not the second nerve, and wherein the pharmaceutical composition comprises multivesicular liposomes comprising: at least one amphipathic lipid, at least one neutral lipid, and bupivacaine phosphate, wherein the bupivacaine phosphate is encapsulated within the multivesicular liposome, thereby administering to the adductor canal of the patient the pharmaceutical composition for post-operative analgesia.

Provided herein are methods of administering to the adductor canal of a human patient a pharmaceutical composition for post-operative analgesia, comprising: (a) selecting an entry point of an injection needle in a leg in a patient by ultrasound transducer; (b) advancing a needle tip of the injection needle within a region between a vastus medialis muscle and a sartorius muscle of the patient along a trajectory that extends between the entry point and a superficial femoral artery; (c) identifying a first nerve in the leg of the patient; (d) administering to the first nerve through the injection needle saline and about 10 mL of a pharmaceutical composition; (e) identifying a second nerve in the leg of the patient; (f) administering to the second nerve through the injection needle saline and about 10 mL of the pharmaceutical composition; wherein the first nerve and second nerve are selected from the group consisting of the nerve to vastus medialis (NVM) and the saphenous nerve, and wherein the first nerve is not the second nerve, and wherein the pharmaceutical composition comprises multivesicular liposomes comprising: at least one amphipathic lipid, at least one neutral lipid, and bupivacaine phosphate, wherein the bupivacaine phosphate is encapsulated within the multivesicular liposome, thereby administering to the adductor canal of the human patient the pharmaceutical composition for post-operative analgesia.

Provided herein are methods of treating post-operative knee pain in a patient, comprising: (a) selecting an entry point of an injection needle in a leg of the patient; (b) inserting the injection needle into the leg of the patient at the entry point; (c) identifying a first nerve in the leg of the patient; (d) administering to the first nerve saline and a pharmaceutical composition; (e) identifying a second nerve in the leg of the patient; (f) administering to the second nerve saline and the pharmaceutical composition; wherein the first nerve and second nerve are selected from the group consisting of the nerve to vastus medialis (NVM) and the saphenous nerve, and wherein the first nerve is not the second nerve, and wherein the pharmaceutical composition comprises multivesicular liposomes comprising: at least one amphipathic lipid, at least one neutral lipid, and bupivacaine phosphate, wherein the bupivacaine phosphate is encapsulated within the multivesicular liposome, thereby treating post-operative knee pain in the patient.

Provided herein are methods of administering an adductor canal block to a patient, comprising: (a) selecting an entry point of an injection needle in a leg of a patient by ultrasound transducer, wherein the entry point comprises a region adjacent to a superficial femoral artery in the middle of a sartorius muscle; (b) advancing a needle tip of the injection needle within a region between a vastus medialis muscle and a sartorius muscle of the patient along a trajectory that extends between the entry point and a superficial femoral artery; (c) identifying a nerve to vastus medialis (NVM) in the patient; (d) administering to the NVM through the injection needle saline and about 10 mL of a multivesicular liposome pharmaceutical composition; (e) identifying a saphenous nerve, wherein identifying a saphenous nerve in the patient comprises penetrating a vasto-adductor membrane with the needle tip and advancing the needle tip to a location anterior to the superficial femoral artery; (f) administering to the saphenous nerve through the injection needle saline and about 10 mL of a multivesicular liposome pharmaceutical composition to the saphenous nerve; wherein the multivesicular liposome pharmaceutical composition comprises: bupivacaine or a salt thereof; phosphoric acid; a lipid component comprising at least one amphipathic lipid and at least one neutral lipid lacking a hydrophilic head group; and, optionally, a cholesterol and/or a plant sterol, thereby administering the adductor canal block to the patient.

Further, in some embodiments the injection needle is connected to a peripheral nerve stimulator (PNS). In some embodiments, the PNS is tuned to 2 hertz and between 0.5 to 1.0 mA. In some embodiments, the PNS is used to identify the first nerve and/or the second nerve. In some embodiments, the PNS is used to identify the first nerve and the second nerve. In some embodiments, the first nerve is the nerve to vastus medialis (NVM) and the second nerve is the saphenous nerve. In some embodiments, identifying the entry point of the injection needle comprises the point at which a superficial femoral artery is in the middle of a sartorius muscle. In some embodiments, the injection needle is a 100 mm, 21-gauge needle. In some embodiments, the injection needle is insulated. In some embodiments, the injection needle into the leg of the patient comprises advancing a needle tip of the injection needle within a region between a vastus medialis muscle and a sartorius muscle of the patient along a trajectory that extends between the entry point and a superficial femoral artery. In some embodiments, the insertion of the injection needle into the leg of the patient does not comprise penetrating a vasto-adductor membrane. In some embodiments, insertion of the injection needle into the leg of the patient comprises penetrating a vasto-adductor membrane with the needle tip and advancing the needle tip to a location anterior to the superficial femoral artery. In some embodiments, the saline injection comprises no more than 1 to 2 mL of saline. In some embodiments, a syringe used for the saline injection is different from a syringe used for the pharmaceutical administration. In some embodiments, administering the pharmaceutical composition comprises administering about 10 mL of the pharmaceutical composition to each of the first nerve and the second nerve. In some embodiments, the method comprises administering about 20 mL total of the pharmaceutical composition. In some embodiments, the multivesicular liposomes comprise: bupivacaine or a salt thereof; phosphoric acid; a lipid component comprising at least one amphipathic lipid and at least one neutral lipid lacking a hydrophilic head group; and, optionally, a cholesterol and/or a plant sterol, wherein said multivesicular liposomes are made by a process comprising: (a) preparing a first aqueous component comprising phosphoric acid; (b) preparing a lipid component comprising at least one organic solvent, at least one amphipathic lipid, and at least one neutral lipid lacking a hydrophilic head group; (c) mixing said first aqueous component and said lipid component to form a water-in-oil emulsion, wherein at least one component comprises bupivacaine or a salt thereof; (d) mixing said water-in-oil emulsion with a second aqueous component to form solvent spherules; and (e) removing the organic solvent from the solvent spherules to form multivesicular liposomes encapsulating bupivacaine phosphate. In some embodiments, the methods further comprise administering local anesthetic in the space between the popliteal artery and the posterior capsule of the knee. In some embodiments, the local anesthetic comprises bupivacaine HCl. In some embodiments, the local anesthetic comprises 15 mL of 0.25% bupivacaine HCl. In some embodiments, administration of the local anesthetic uses a 100 mm insulated needle. In some embodiments, the space between the popliteal artery and the posterior capsule of the knee is determined by ultrasound. In some embodiments, administration of the local anesthetic includes administration anterior to the popliteal artery.

BRIEF DESCRIPTION OF THE DRAWINGS

FIG. 3 shows Table 1, a summary of the demographics of the participants of clinical trial #1.

FIG. 4 shows Table 2, a summary of the baseline characteristics of the participants in clinical trial #1.

FIG. 5 shows the time and events schedule of study procedures (screening through POD 14).

FIG. 6 shows Table 3, a summary of the area under the curve of numeric rating scale (NRS) pain intensity score at 0-96 hours post-surgery for participants in clinical trial #1.

FIG. 7 shows Table 4, a summary of the area under the curve of numeric rating scale (NRS) pain intensity score by time interval for participants in clinical trial #1.

FIG. 8 shows Table 5, a summary of total opioid consumption by time interval for participants in clinical trial #1.

FIG. 9 shows Table 6, a summary of time to first opioid consumption post-surgery for participants in clinical trial #1.

FIG. 10 shows Table 7, a summary of the worst and average numeric rating scale pain intensity scores over the last 24 hours from post-surgery day 1 through day 14 for participants in clinical trial #1.

FIG. 13 shows Table 8, a summary of pharmacokinetic (PK) parameters for EXPAREL-admix patients and bupivacaine hydrochloride alone patients for participants in clinical trial #1.

FIG. 14 shows Table 9, a summary of time to onset and duration of motor and sensory block for EXPAREL-admix patients and bupivacaine hydrochloride alone patients for participants in clinical trial #1.

FIG. 15 shows Table 10, an overview of treatment-emergent adverse events between EXPAREL-admix patients and bupivacaine hydrochloride alone patients for participants in clinical trial #1.

FIG. 16 shows Table 11, a summary of treatment-emergent adverse events occurring in ≥5% of subjects in any cohort for participants in clinical trial #1.

DETAILED DESCRIPTION

Figure 1:
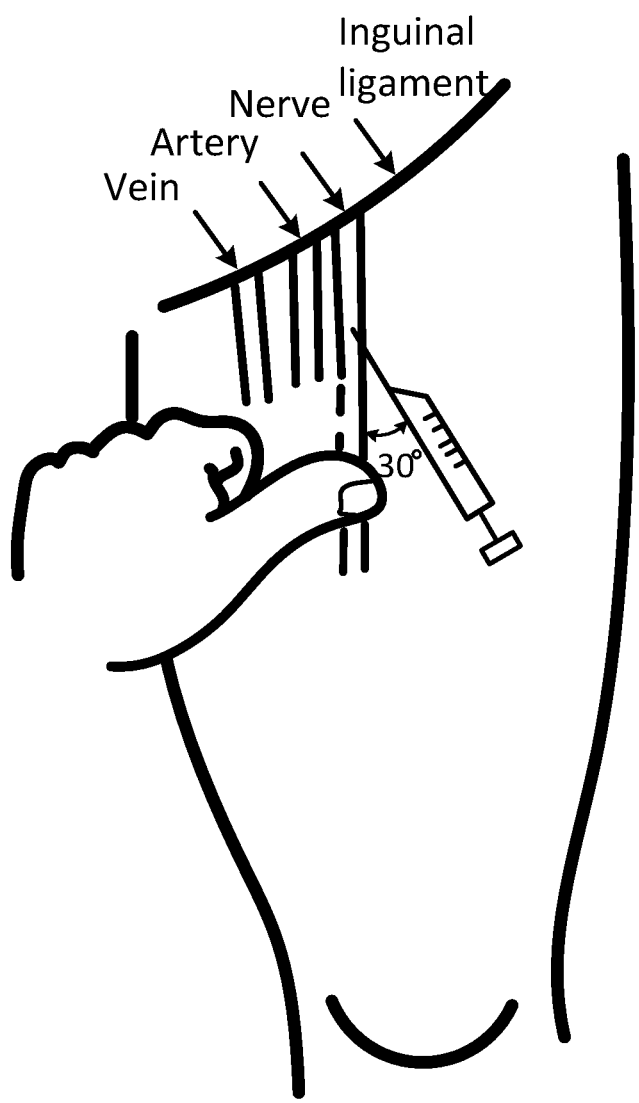
FIG. 1 shows a schematic of an exemplary injection location for a femoral nerve block.
Figure 2:
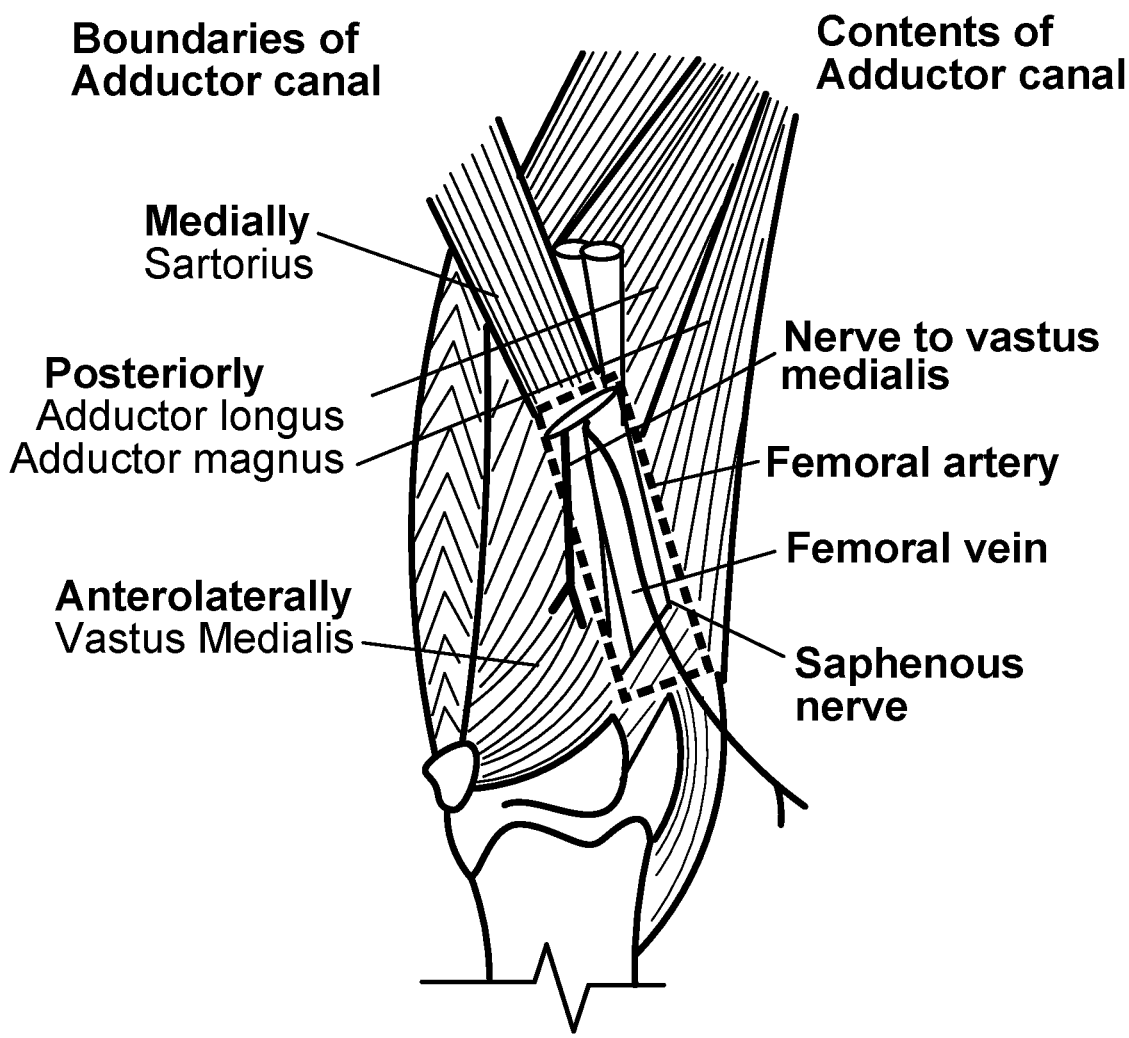
FIG. 2 shows a schematic of an exemplary injection location for an adductor canal block.
Figure 11:
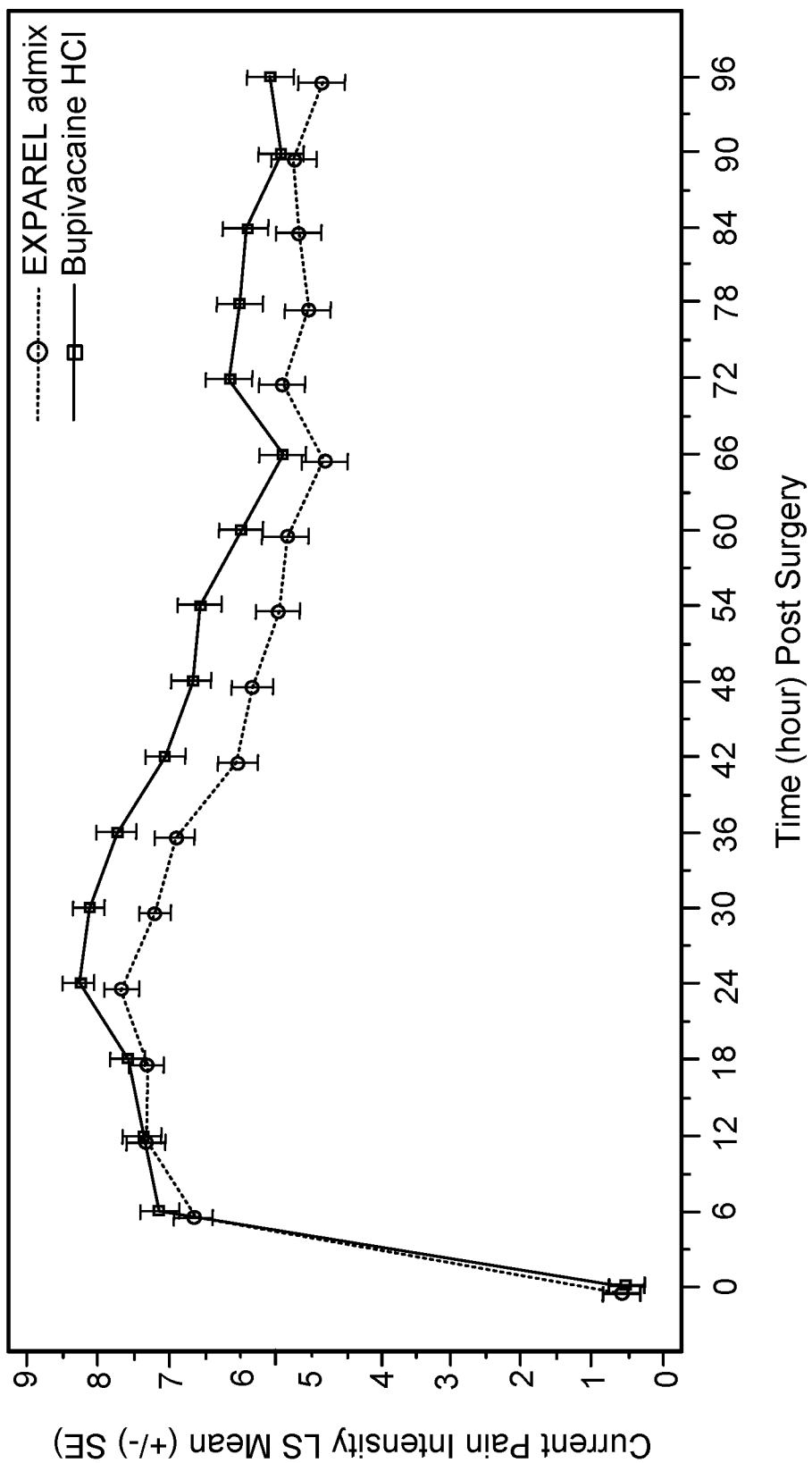
FIG. 11 shows pain intensity between 0 and 96 hours, between EXPAREL admixed with bupivacaine hydrochloride (HCl; round circles) and bupivacaine HCl alone (plus signs) for participants in clinical trial #1. Patients receiving EXPAREL report less pain starting at approximately 18 hours after surgery.
Figure 12:
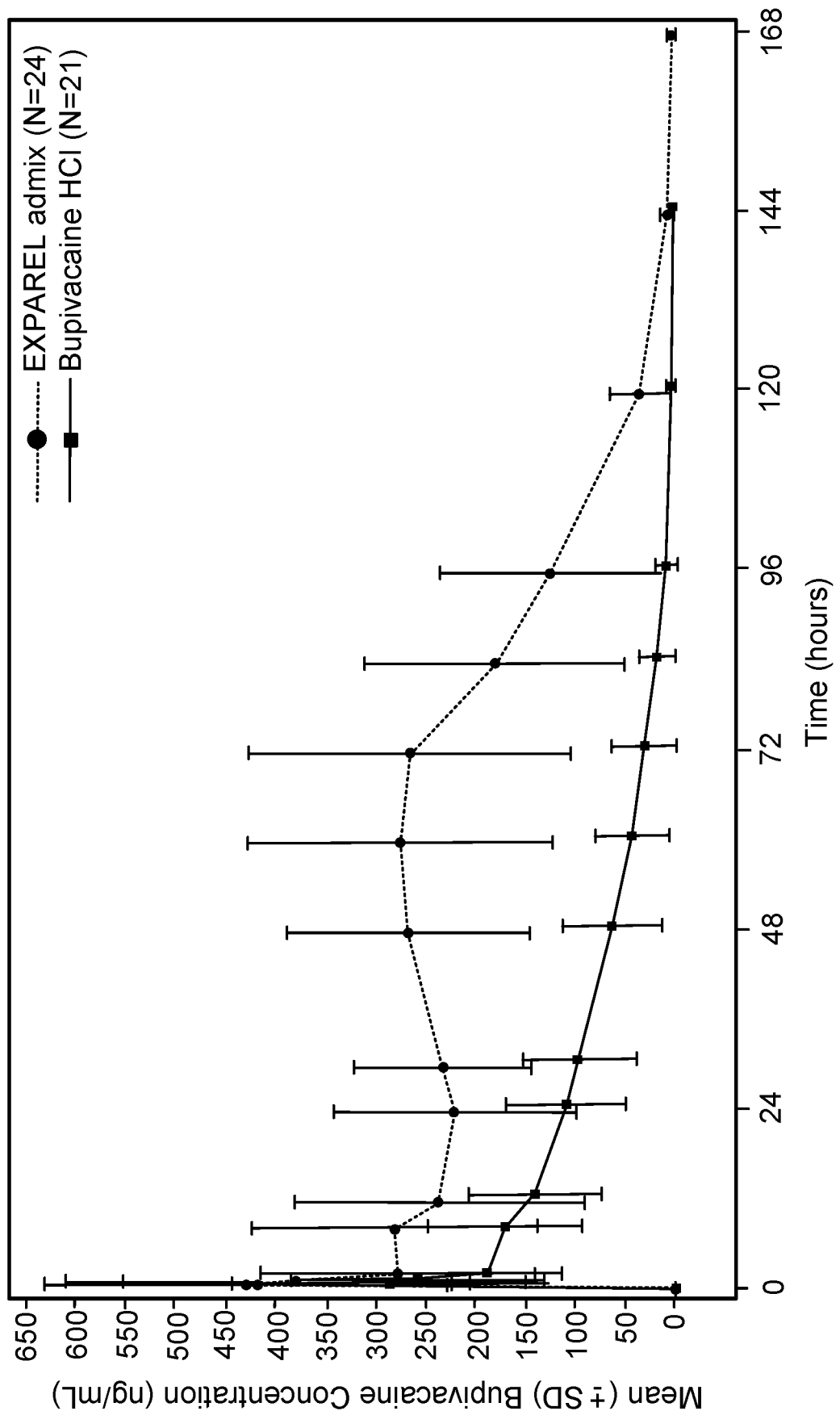
FIG. 12 shows mean bupivacaine concentration over time. Subjects receiving EXPAREL admixed with bupivacaine hydrochloride exhibit an early and a late $C_{max}$, whereas a single peak in PK for those receiving bupivacaine hydrochloride alone for participants in clinical trial #1.

Unless otherwise defined, all technical and scientific terms used herein have the same meaning as commonly understood by one of ordinary skill in the art to which this disclosure belongs. Although methods and materials similar to those described herein can be used in the practice or testing of the present disclosure, suitable methods and materials are described below. All publications, patent applications, patents, and other references mentioned herein are incorporated by reference in their entirety. In addition, the materials, methods, and examples are illustrative only and not intended to be limiting.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "pain" means a physiologic and/or psychologic reaction or response to potential or actual stimulus that may result in tissue damage, injury, disease, or other condition(s). Types of pain include but are not limited to acute pain, chronic pain, thermal pain, traumatic pain, chemical pain, inflammatory pain, ischemic pain, blunt pain, sharp pain, prickling pain, visceral pain, and neuropathic pain.

Adductor Canal/Adductor Canal Block

In some embodiments, the method includes administering a pharmaceutical composition to the adductor canal. In some embodiments, the adductor canal can be described as a conical musculoaponeurotic tunnel passing through the distal portion of the middle third of the thigh. In some embodiments, the adductor canal has three borders: the vastus medialis muscle forms the anterolateral border, the adductor longus and adductor magnus muscles form the posterolateral border, and the sartorius forms the medial wall. Major structures passing through the adductor canal include the superficial femoral artery, the femoral vein, and the saphenous nerve. The adductor canal (subsartorial canal or Hunter's canal) is about 15 cm in length and is a narrow, fascial tunnel in the thigh. The adductor canal is located deep to the middle third of the sartorius muscle. The adductor canal provides an intermuscular passage through which the femoral vessels pass to reach the popliteal fossa, where these vessels become popliteal vessels. The adductor canal begins about 15 cm (about 6 inches) inferior to the inguinal ligament, where the sartorius muscle crosses over the adductor longus muscle. The adductor canal ends at the adductor hiatus in the tendon of the adductor magnus muscle. The saphenous nerve and, in part, the obturator nerve traverse the adductor canal.

In some embodiments, administering a pharmaceutical composition to the adductor canal includes an adductor canal block. In some embodiments, administering a pharmaceutical composition to the adductor canal can be an injection into the femoral triangle. In some embodiments, administering a pharmaceutical composition to the adductor canal includes a "femoral triangle block." In some embodiments, an adductor canal block can be used to deliver sensory anesthesia for procedures involving the distal thigh and femur, knee, and lower leg on the medial side. In some embodiments, an adductor canal block can be used to deliver sensory anesthesia for distal branches of the femoral nerve including the saphenous nerve and branches of the mixed sensory and motor nerves to the quadriceps, and branches of the obturator nerve. In some embodiments, administering a pharmaceutical composition to the adductor canal can be the administration of a sensory nerve block only, and not a motor nerve block. In some embodiments, the adductor canal is located in the middle third of the thigh. In some embodiments the adductor canal is lower on the leg than the location for a femoral nerve block. In some embodiments, the location for an adductor canal block is inferior to the location for a femoral nerve block. In some embodiments, the location for an adductor canal block is distal to the location for a femoral nerve block. In some embodiments, the location for an adductor canal block is medial to the location for a femoral nerve block.

In some embodiments, the adductor canal can be located by way of surface landmarks. In some embodiments, the adductor canal can be located by way of ultrasound guidance. In some embodiments, the adductor canal can be located by way of a combination of surface landmarks and ultrasound guidance. In some embodiments, an adductor canal block preserves quadriceps muscle strength better than a femoral nerve block. In some embodiments, an adductor canal block preserves ambulation compared to femoral nerve block. In some embodiments, an adductor canal block reduces falls compared to a femoral nerve block. In some embodiments, an adductor canal block facilitates postoperative rehabilitation compared to a femoral nerve block.

Femoral Nerve/Femoral Nerve Block

In some embodiments, administration of a pharmaceutical composition to the adductor canal is not equivalent to administration of a pharmaceutical composition to the location for a femoral nerve block. In some embodiments, the methods of administering pharmaceutical compositions described herein, including those administering a pharmaceutical composition to the adductor canal, are not administered to location of a femoral nerve block. In some embodiments, the methods of administering pharmaceutical compositions described herein, including those administering a pharmaceutical composition to the adductor canal, do not include administering a femoral nerve block.

The anatomical location for administration of a femoral nerve block can include: identifying the inguinal ligament by drawing a line between the anterior superior iliac spine and the pubic symphysis. The femoral nerve passes through the center of this line and is at its most superficial at the level of the inguinal crease. In some embodiments, the location for a femoral nerve block is located near the hip. In some embodiments, the location for a femoral nerve block is higher on the leg than the location for an adductor canal block. In some embodiments, the location for a femoral nerve block is superior to the location of an adductor canal block. In some embodiments, the location for a femoral nerve block is proximal to the location of an adductor canal block. In some embodiments, the location for a femoral nerve block is lateral to the location of an adductor canal block.

In some embodiments, the location for a femoral nerve block can be located by way of surface landmarks. In some embodiments, the location for a femoral nerve block can be located by way of ultrasound guidance. In some embodiments, the location for a femoral nerve block can be located by way of a combination of surface landmarks and ultrasound guidance. In some embodiments, a femoral nerve block leads to a decrease in quadriceps muscle strength over an adductor canal block. In some embodiments, a femoral nerve block leads to more impaired ambulation over an adductor canal block. In some embodiments, a femoral nerve block leads to more post-operative falls than an adductor canal block. In some embodiments, a femoral nerve block requires greater postoperative rehabilitation compared to an adductor canal block.

Pharmaceutical Compositions

Provided herein are analgesic pharmaceutical compositions. In some embodiments the pharmaceutical compositions can be used for post-operative analgesic pain.

In some embodiments, the pharmaceutical compositions include multivesicular liposomes. Multivesicular liposomes (or "MVL", which is used herein to refer to a multivesicular liposome or a plurality of multivesicular liposomes) are lipid vesicles having multiple non-concentric internal aqueous chambers having internal membranes distributed as a network throughout the MVL. The chambers may contain acids which are effective to enable the encapsulation of bupivacaine or a salt thereof and to modulate its release rate. A preparation of MVL is described, for example, in Kim et al., Biochim. Biophys. Acta 728, 339-348, 1983. In some embodiments, a MVL is prepared in accordance with a process as described in U.S. Pat. No. 9,192,575, incorporated by reference herein in its entirety. In some embodiments, a MVL is prepared in accordance with a process as described in U.S. Pat. No. 8,182,835, incorporated by reference herein in its entirety. In some embodiments, a MVL is prepared in accordance with a process as described in U.S. Pat. No. 8,834,921, incorporated by reference herein in its entirety. In some embodiments, a MVL is prepared in accordance with a process as described in U.S. Pat. No. 9,205,052, incorporated by reference herein in its entirety.

In some embodiments the multivesicular liposomes ("MVL") are made by the following process. A "water-in-oil" type emulsion containing a non-hydrohalic acid salt of bupivacaine, such as bupivacaine phosphate, is formed from two immiscible phases, a lipid phase and a first aqueous phase. The lipid phase is made up of at least one amphipathic lipid and at least one neutral lipid in a volatile organic solvent. The term "amphipathic lipid" refers to molecules having a hydrophilic "head" group and a hydrophobic "tail" group and may have membrane-forming capability. As used herein, amphipathic lipids include those having a net negative charge, a net positive charge, and zwitterionic lipids (having no net charge at their isoelectric point). The term "neutral lipid" refers to oils or fats that have no vesicle-forming capability by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes.

The amphipathic lipid is chosen from a wide range of lipids having a hydrophobic region and a hydrophilic region in the same molecule. Suitable amphipathic lipids are zwitterionic phospholipids, including phosphatidylcholines, phosphatidylethanolamines, sphingomyelins, lysophosphatidylcholines, and lysophosphatidylethanolamines. Also suitable are the anionic amphipathic phospholipids such as phosphatidylglycerols, phosphatidylserines, phosphatidylinositols, phosphatidic acids, and cardiolipins. Also suitable are the cationic amphipathic lipids such as acyl trimethylammonium propanes, diacyl dimethylammonium propanes, and stearylamines.

Suitable neutral lipids are triglycerides, propylene glycol esters, ethylene glycol esters, and squalene. Examples of triglycerides useful in the present disclosure are triolein, tripalmitolein, trimyristolein, trilinolein, tributyrin, tricaproin, tricaprylin, and tricaprin. The fatty chains in the triglycerides useful in the present disclosure can be all the same, or not all the same (mixed chain triglycerides), including all different. Both saturated and unsaturated fatty chains are useful in the present disclosure. The propylene glycol esters can be mixed diesters of caprylic and capric acids.

Many types of volatile organic solvents can be used in the present disclosure, including ethers, esters, halogenated ethers, hydrocarbons, halohydrocarbons, or Freons. For example, diethyl ether, chloroform, tetrahydrofuran, ethyl acetate, Forane, and any combinations thereof are suitable for use in making the compositions of the present disclosure.

Optionally, other components are included in the lipid phase. Among these are cholesterol or plant sterols.

The first aqueous phase includes bupivacaine or a salt thereof, such as bupivacaine phosphate, at least one polyhydroxy carboxylic acid, and at least one di- or tri-protic mineral acid. In some embodiments, also included is hydrochloric acid. The di- or tri-protic mineral acids include sulfuric acid, and phosphoric acid. Also included in the first aqueous phase are such polyhydroxy carboxylic acids as glucuronic acid, gluconic acid, and tartaric acid. The di- and tri-protic mineral acids and the polyhydroxy organic acids are present in the first aqueous phase in concentrations of from 0.01 mM to about 0.5 M, or preferably from about 5 mM to about 300 mM. When hydrochloric acid is used, it is present in lower amounts, from about 0.1 mM to about 50 mM, or preferably from about 0.5 mM to about 25 mM.

The lipid phase and first aqueous phase are mixed by mechanical turbulence, such as through use of rotating or vibrating blades, shaking, extrusion through baffled structures or porous pipes, by ultrasound, or by nozzle atomization, to produce a water-in-oil emulsion. Thus, bupivacaine or a salt thereof, such as bupivacaine phosphate, is encapsulated directly in the first step of MVL manufacture.

The whole water-in-oil emulsion is then dispersed into a second aqueous phase by means described above, to form solvent spherules suspended in the second aqueous phase. The term "solvent spherules" refers to a microscopic spheroid droplet of organic solvent, within which are suspended multiple smaller droplets of aqueous solution. The resulting solvent spherules therefore contain multiple aqueous droplets with the bupivacaine or a salt thereof, such as bupivacaine phosphate, dissolved therein. The second aqueous phase can contain additional components such as glucose, and/or lysine.

The volatile organic solvent is then removed from the spherules, for instance by surface evaporation from the suspension: When the solvent is substantially or completely evaporated, MVL are formed. Gases which can be used for the evaporation include nitrogen, argon, helium, oxygen, hydrogen, and carbon dioxide. Alternatively, the volatile solvent can be removed by sparging, rotary evaporation, or with the use of solvent selective membranes.

In some embodiments, an MVL is prepared in accordance with a process as described in U.S. Pat. No. 10,398,648, incorporated by reference herein in its entirety. In some embodiments, a MVL is prepared in accordance with a process as described in U.S. Pat. No. 9,585,838 incorporated by reference herein in its entirety.

In some embodiments, an MVL is prepared in accordance with a process as described in US Published Patent Applications US 2011-0250264, US 2013-0306759, US 2013-0177634, US 2013-0177633, US 2013-0177635, US 2013-0195965, US 2013-0177636, US 2013-0183373, US 2013-0177638, US 2013-0177637, US 2013-0183372, US 2013-0183375, US 2016-0361260 or US 2018-0092847, each of which is incorporated by reference herein in its entirety.

In some embodiments, an MVL is prepared in accordance with a process as described in U.S. Pat. Nos. 11,033,495; 11,179,336; 11,278,494; 11,304,904; 11,311,486; 11,357,727; 11,426,348; 11,452,691, each of which is incorporated by reference herein in its entirety.

In some embodiments, the pharmaceutical compositions described herein can be combined, used in conjunction with, or used in an anesthetic or analgesic program with other anesthetics or analgesics.

Examples of anesthetics, include but are not limited to, propofol, etomidate, methohexital and sodium thiopental, midazolam, diazepam, and ketamine, benzocaine, chloroprocaine, cocaine, cyclomethycaine, dimethocaine, propoxycaine, procaine, proparacaine, tetracaine, articaine, bupivacaine, carticaine, dibucaine, etidocaine, levobupivacaine, lidocaine, mepivacaine, piperocaine, prilocaine, ropivacaine, trimecaine, saxitoxin, and tetrodotoxin. Examples of amide anesthetics, include but are not limited to, articaine, bupivacaine, carticaine, dibucaine, etidocaine, levobupivacaine, lidocaine, mepivacaine, piperocaine, prilocaine, ropivacaine, and trimecaine. In some embodiments, the multivesicular liposomes further comprise bupivacaine, morphine, cytarabine, or their pharmaceutically acceptable salts as the therapeutic agent. In some embodiments, the multivesicular liposomes further comprise bupivacaine phosphate, morphine sulfate, or cytarabine HCl.

The term "therapeutically effective" as it pertains to bupivacaine or a salt thereof, such as bupivacaine phosphate, present in the pharmaceutical compositions described herein, means that an anesthetic present in the first aqueous phase within the multivesicular liposome is released in a manner sufficient to achieve a particular level of anesthesia. Exact dosages will vary depending on such factors as the particular anesthetic, as well as patient factors such as age, sex, general condition, patient size, and the like. Those of skill in the art can readily take these factors into account and use them to establish effective therapeutic concentrations without resort to undue experimentation.

As used herein, "non-liposomal bupivacaine" refers to bupivacaine or a salt thereof that is not in liposomal form. For example, "non-liposomal bupivacaine" refers to bupivacaine or a salt thereof that is not comprised in a multivesicular liposome. The term "non-liposomal bupivacaine" encompasses compositions comprising bupivacaine, or a salt thereof, that is not in liposomal form.

Examples of analgesics can include opioid analgesics and non-opioid analgesics. Non-limiting examples of opioid analgesics include hydrocodone, oxycodone, propoxyphene, or fentanyl, thiosemicarbazone, p-nitrophenylhydrazone, o-methyloxime, semicarbazone, or bis (methylcarbamate), oxycodone, a pharmaceutically acceptable salt or its thiosemicarbazone, p-nitrophenylhydrazone, o-methyloxime, semicarbazone, or bis-methylcarbamate. Non-limiting examples of non-opioid analgesics useful in the present invention include aspirin; acetaminophen; a non-steroidal anti-inflammatory drug (NSAID), an arylalkanoic acid, a profen, a fenamic acid, an oxicam, a pyrazolidine derivative; a Cox-2 inhibitor, a local analgesic, an anti-depressant, an atypical analgesic, a psychotropic agent, an NMDA receptor antagonist, an α2-adrenoreceptor agonists and a synthetic drug having narcotic properties.

Embodiments of the present disclosure also include compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Academic Press, (Adeboye Adejareedit edit., 2020), hereby incorporated by reference in its entirety.

A pharmaceutically effective dose is that dose required to prevent, inhibit the occurrence, or treat (alleviate a symptom to some extent, preferably all of the symptoms) pain. One skilled in the art appreciates that compositions and methods of the present disclosure can be used to treat multiple types of pain, and that the effective dose may be different for different types of pain. Types of pain include but are not limited to thermal pain, chemical pain, inflammatory pain, ischemic pain, trauamatic pain, blunt pain, sharp pain, prickling pain, and visceral pain. The pharmaceutically effective dose depends on the type of condition (e.g., pain), the composition used, the route of administration, the type of mammal being treated, the physical characteristics of the specific mammal under consideration (including but not limited to age, physical condition, surgical or other medical procedures being performed, circulatory capacity, cardiovascular function, pain tolerance, nerve function, liver function), concurrent medication, and other factors that those skilled in the medical arts will recognize.

Methods of Administering

Provided herein are methods of administering an adductor canal block. In some embodiments, the methods include administering to the adductor canal of a patient a pharmaceutical composition for post-operative analgesia, comprising: (a) selecting an entry point of an injection needle in a leg of a patient by ultrasound transducer; (b) inserting the injection needle into the patient at the entry point; (c) identifying a first nerve in the leg of the patient; (d) administering to the first nerve saline and a pharmaceutical composition; (e) identifying a second nerve in the leg of the patient; (f) administering to the second nerve saline and the pharmaceutical composition; wherein the first nerve and second nerve are selected from the group consisting of the nerve to vastus medialis (NVM) and the saphenous nerve, and wherein the first nerve is not the second nerve, and wherein the pharmaceutical composition comprises multivesicular liposomes comprising: at least one amphipathic lipid, at least one neutral lipid, and bupivacaine phosphate, wherein the bupivacaine phosphate is encapsulated within the multivesicular liposome, thereby administering to the adductor canal of the patient the pharmaceutical composition for post-operative analgesia.

In some embodiments, the methods include administering to the adductor canal of a human patient a pharmaceutical composition for post-operative analgesia, comprising: (a) selecting an entry point of an injection needle in a leg in a patient by ultrasound transducer; (b) advancing a needle tip of the injection needle within a region between a vastus medialis muscle and a sartorius muscle of the patient along a trajectory that extends between the entry point and a superficial femoral artery; (c) identifying a first nerve in the leg of the patient; (d) administering to the first nerve through the injection needle saline and about 10 mL of a pharmaceutical composition; (e) identifying a second nerve in the leg of the patient; (f) administering to the second nerve through the injection needle saline and about 10 mL of the pharmaceutical composition; wherein the first nerve and second nerve are selected from the group consisting of the nerve to vastus medialis (NVM) and the saphenous nerve, and wherein the first nerve is not the second nerve, and wherein the pharmaceutical composition comprises multivesicular liposomes comprising: at least one amphipathic lipid, at least one neutral lipid, and bupivacaine phosphate, wherein the bupivacaine phosphate is encapsulated within the multivesicular liposome, thereby administering to the adductor canal of the human patient the pharmaceutical composition for post-operative analgesia.

In some embodiments, the methods include treating post-operative knee pain in a patient, comprising: (a) selecting an entry point of an injection needle in a leg of the patient; (b) inserting the injection needle into the leg of the patient at the entry point; (c) identifying a first nerve in the leg of the patient; (d) administering to the first nerve saline and a pharmaceutical composition; (e) identifying a second nerve in the leg of the patient; (f) administering to the second nerve saline and the pharmaceutical composition; wherein the first nerve and second nerve are selected from the group consisting of the nerve to vastus medialis (NVM) and the saphenous nerve, and wherein the first nerve is not the second nerve, and wherein the pharmaceutical composition comprises multivesicular liposomes comprising: at least one amphipathic lipid, at least one neutral lipid, and bupivacaine phosphate, wherein the bupivacaine phosphate is encapsulated within the multivesicular liposome, thereby treating post-operative knee pain in the patient.

In some embodiments, the methods include, administering an adductor canal block to a patient, comprising: (a) selecting an entry point of an injection needle in a leg of a patient by ultrasound transducer, wherein the entry point comprises a region adjacent to a superficial femoral artery in the middle of a sartorius muscle; (b) advancing a needle tip of the injection needle within a region between a vastus medialis muscle and a sartorius muscle of the patient along a trajectory that extends between the entry point and a superficial femoral artery; (c) identifying a nerve to vastus medialis (NVM) in the patient; (d) administering to the NVM through the injection needle saline and about 10 mL of a multivesicular liposome pharmaceutical composition; (e) identifying a saphenous nerve, wherein identifying a saphenous nerve in the patient comprises penetrating a vasto-adductor membrane with the needle tip and advancing the needle tip to a location anterior to the superficial femoral artery; (f) administering to the saphenous nerve through the injection needle saline and about 10 mL of a multivesicular liposome pharmaceutical composition to the saphenous nerve; wherein the multivesicular liposome pharmaceutical composition comprises: bupivacaine or a salt thereof; phosphoric acid; a lipid component comprising at least one amphipathic lipid and at least one neutral lipid lacking a hydrophilic head group; and, optionally, a cholesterol and/or a plant sterol, thereby administering the adductor canal block to the patient.

Further, these methods can also be administered to a patient for treating knee pain associated with total knee arthroplasty, reducing an amount of post-operative pain in a patient following total knee arthroplasty surgery, reducing an amount of an opioid analgesic administered to a patient following total knee arthroplasty surgery, administering to the adductor canal of a patient a pharmaceutical composition, or administering to the adductor canal of a patient a pharmaceutical composition for the management of post-operative pain associated with total knee arthroplasty.

Routes of Administration

Anesthetics of the present disclosure may be delivered regionally or locally. "Regional" or "local" anesthesia, as used herein, is distinct from general anesthesia and refers to anesthetic procedures which allow for the preferential delivery of an anesthetic to a specific region of the body, such as near a nerve or a nerve bundle. In contrast, general anesthesia allows for the systemic administration of an anesthetic, e.g., via intravenous administration. Regional or local anesthesia typically allows for a lower total body concentration (although elevated local concentrations) of an anesthetic to be administered to a subject for analgesia or diminished pain perception of at least a portion of the subject's body. For example, intrathecal anesthesia, epidural anesthesia, and nerve blocks are examples of regional or local anesthesia.

A pharmacological composition can refer to a composition in a form suitable for administration, e.g., perineural administration, into a subject or proximal to at least one nerve of a subject, including for example wherein the subject is a human. Suitable forms, in part, depend upon the use or the route of entry. Examples of routes of entry include but are not limited to injection (including but not limited to subcutaneous injection), single injection, serial injection, indwelling catheter, and continuous infusion. Such routes of entry should not prevent the composition from reaching a target cell (i.e., a neuron). For example, injectable pharmacological compositions should be soluble. Other factors are known in the art, and include considerations such as toxicity and forms that prevent the composition or formulation from exerting its effect.

EXAMPLES

Example 1—Clinical Trial #1

A multicenter, randomized, double-blind clinical trial examining efficacy and safety of the pharmaceutical composition comprising: a) the multivesicular liposome disclosed herein and b) the aqueous phase disclosed herein, wherein the aqueous phase is encapsulated within the multivesicular liposome, was performed as described below. The pharmaceutical composition is referred to below as the "multivesicular liposomal" pharmaceutical composition, or "MVL".

The trial compared the magnitude of the postsurgical analgesic effect following a single dose of the MVL admixed with bupivacaine HCl vs. bupivacaine HCl when administered via an adductor canal block in subjects undergoing primary unilateral TKA. Further, the trial compared post-surgical opioid consumption following a single dose of MVL admixed with bupivacaine HCl vs. bupivacaine HCl. Additionally, the trial compared the time to first opioid consumption post-surgery, following a single dose of MVL admixed with bupivacaine HCl vs. bupivacaine HCl. Additionally, the trial characterized and compared the magnitude of the duration of sensory and motor block following a single dose of MVL admixed with bupivacaine HCl and bupivacaine HCl. Further, the trial assessed the safety and PK profile of MVL admixed with bupivacaine HCl and bupivacaine HCl.

| Abbreviation/ Term | Definition |
|---|---|
| $\lambda_z$ | Apparent terminal elimination constant rate |
| AE | Adverse event |
| AESI | Adverse event of special interest |
| ANCOVA | Analysis of covariance |
| ASA | American Society of Anesthesiologists |
| AUC | Area under the curve |
| $AUC_{0-\infty}$ | Area under the curve from the time of dosing to infinity |
| $AUC_{0-last}$ | Area under the curve from the time of dosing to the last quantifiable concentration |
| $AUC_{extr}$ | Extrapolated area under the curve from time of last point above lower limit of quantification to infinity |
| BLOQ | Below the limit of quantification |
| BMI | Body mass index |
| CFR | Code of Federal Regulations |
| CI | Confidence interval |
| CL/F | Apparent clearance |
| $C_{max}$ | Maximum plasma concentration |
| $C_t$ | The last quantifiable concentration |
| CV | Coefficient of variation |
| Diff | Difference |
| eCRF | Electronic case report form |
| EKG | Electrocardiogram |
| FDA | Food and Drug Administration |
| GCP | Good Clinical Practice |
| h | Hour(s) |

| Abbreviation/Term | Definition |
|---|---|
| $H_a$ | Alternative hypothesis |
| HCF | Health care facility |
| HCl | Hydrochloride |
| ICF | Informed consent form |
| ICH | International Council for Harmonisation |
| ID | Identification |
| IEC | Independent Ethics Committee |
| Intra-op | During operation |
| IPACK | Infiltration between the popliteal artery and the posterior capsule of the knee |
| IPO | International Pain Outcome |
| IRB | Institutional Review Board |
| IV | Intravenous(ly) |
| LLOQ | Lower limit of quantification |
| LSM | Least squares (mean) |
| Max | Maximum |
| MedDRA | Medical Dictionary for Regulatory Activities |
| Min | Minimum |
| min | Minute(s) |
| NA | Not applicable |
| NCA | Noncompartmental analysis |
| NE | Not estimatable |
| NRS | Numeric Rating Scale |
| NSAID | Non-steroidal anti-inflammatory drug |
| OMED | Oral morphine equivalents |
| OR | Operating Room |
| PACU | Post-anesthesia Care Unit |
| PD | Pharmacodynamic |
| PK | Pharmacokinetic |
| PO | Orally administered |
| POD | Post-operative day |
| Post-op | Post-operative |
| Pre-op | Pre-operative |
| PT | Preferred term |
| Reduct | Reduction |
| SAE | Serious adverse event |
| SAP | Statistical Analysis Plan |
| SD | Standard deviation |
| SE | Standard error |
| SOC | System organ class |
| $t_{1/2el}$ | Apparent terminal elimination half-life |
| TEAE | Treatment-emergent adverse event |
| TKA | Total knee arthroplasty |
| $T_{max}$ | Time of maximum plasma concentration |
| $V_d/F$ | Apparent volume of distribution |
| WOCBP | Women of childbearing potential |

Inclusion Criteria

Each subject had to meet the following criteria to be eligible for the study:
1. Male or female, ages 18 or older at screening.
2. Indicated to undergo primary unilateral TKA under spinal anesthesia.
3. Primary indication for TKA was degenerative osteoarthritis of the knee.
4. American Society of Anesthesiologists (ASA) physical status 1, 2, or 3 (see Section 18.5 of the Protocol [Section 16.1.1]).
5. Able to provide informed consent, adhere to the study schedule, and complete all study assessments.
6. Body mass index≥18 and <40 kg/m2.

Exclusion Criteria

Subjects who met any of the following criteria were excluded from the study:
1. Allergy, hypersensitivity, intolerance, or contraindication to any of the study medications for which an alternative was not named in the Protocol (e.g., amide-type local anesthetics, opioids, bupivacaine HCl, non steroidal anti inflammatory drugs [NSAIDs]).
2. Planned concurrent surgical procedure (e.g., bilateral TKA).
3. Undergoing unicompartmental TKA or revision TKA.
4. Concurrent painful physical condition (e.g., arthritis, fibromyalgia, cancer) that may have required analgesic treatment with NSAIDs or opioids in the post dosing period for pain that were not strictly related to the knee surgery and which, in the Investigator's opinion, may have confounded the post dosing assessments.
5. Inadequate sensory function below the knee as assessed by the Investigator.
6. History of contralateral TKA within 1 year.
7. Previous open knee surgery on the knee being considered for TKA. Prior arthroscopy was permitted.
8. History of, suspected, or known addiction to or abuse of illicit drug(s), prescription medicine(s), or alcohol within the past 2 years.
9. Administration of an investigational drug within 30 days or 5 elimination half-lives of such investigational drug, whichever was longer, prior to study drug administration, or planned administration of another investigational product or procedure during the subject's participation in this study.
10. Previous participation in an EXPAREL study.
11. Uncontrolled anxiety, schizophrenia, or other psychiatric disorder that, in the opinion of the Investigator, could have interfered with study assessments or compliance.
12. Currently pregnant, nursing, or planning to become pregnant during the study.
13. Clinically significant medical disease that, in the opinion of the Investigator, would have made participation in a clinical study inappropriate. This included diabetic neuropathy, coagulation or bleeding disorders, severe peripheral vascular disease, renal insufficiency, hepatic dysfunction or other conditions that would have constituted a contraindication to participation in the study.
14. Currently on a neuromodulating agent (e.g., gabapentin, pregabalin [Lyrica®], duloxetine [Cymbalta®], etc.)].
15. Current use of systemic glucocorticoids within 30 days of randomization in this study.
16. Use of dexmedetomidine HCl (Precedex®) or clonidine within 3 days of study drug administration.
17. Any use of marijuana (including tetrahydrocannabinol and cannabidiol) within 30 days prior to randomization, or planned use during the course of the study.
18. Chronic opioid use (average ≥30 OMED/day) within 30 days prior to randomization.

Methods

This was a Phase 3, multicenter, randomized, double blind, active controlled study of 167 subjects undergoing primary unilateral TKA under spinal anesthesia. The study consisted of 2 cohorts that were enrolled in parallel. Cohort 1 enrolled 46 subjects to obtain information on the PK profile, pharmacodynamics (PD), efficacy, and safety. Cohort 2 enrolled 121 subjects to obtain information on efficacy and safety. An adaptive study design was used in this study, with an interim analysis conducted by an unblinded independent review committee to evaluate sample size assumptions and futility.

Subject participation began upon obtaining informed consent, which was obtained within ≤45 days prior to administration of the study drug. Screening procedures included assessment of eligibility; recording of medical/surgical history, prior and concomitant medications (related to medical history), demographics and baseline characteristics, and height and weight for body mass index (BMI) calculation;

assessment of chronic opioid and any *Cannabis* use in the past 30 days (average ≥30 OMED/day); urine pregnancy test for women of childbearing potential (WOCBP); 12-lead electrocardiogram (EKG); and monitoring of adverse events (AEs) and serious adverse events (SAEs).

On the day of surgery, prior to surgery, subjects in Cohort 1 and Cohort 2 were randomized (1:1) to receive an adductor canal block with a single dose of either 10 mL EXPAREL (133 mg) admixed with 10 mL 0.5% bupivacaine HCl (50 mg; from hereon referred to as the EXP133-ADMIX arm) or 10 mL 0.5% bupivacaine HCl (50 mg) mixed with 10 mL normal saline (from hereon referred to as the BUP50 arm). The total dose volume was consistent (20 mL) for all subjects.

Subjects may have been lightly sedated with 1 to 2 mg of intravenous (IV) midazolam before the nerve block procedure. The study drug was administered under ultrasound guidance 90 (±30) min prior to surgery. A peripheral nerve stimulator was used to confirm nerves in the adductor canal before study drug administration. A confirmatory ultrasound video was captured during the nerve block procedure (during hydrodissection by saline injection and study drug administration), with needle in place to ensure accurate block placement. All subjects in both Cohort 1 and Cohort 2 received an infiltration between the popliteal artery and capsule of the knee under ultrasound guidance with 15 mL of 0.25% bupivacaine HCl (37.5 mg) immediately following study drug administration (IPACK infiltration procedure).

Treatment prior to study drug administration may include Celecoxib 200 mg orally administered within 4 hours prior to surgery. Other permitted prior medications and therapy may include 1 to 2 mg of midazolam and/or ondansetron. Restricted medications and therapy prior to drug study administration included systemic glucocorticosteroids and neuromodulating agents (e.g., gabapentin, pregabalin [Lyrica®], duloxetine [Cymbalta®], etc.); no long-acting or sustained release opioid medications and NSAIDs (except for low-dose acetylsalicylic acid used for cardiovascular protection) within 3 days of study drug administration; no dexmedetomidine HCl (Precedex®) or clonidine within 3 days of study drug administration; no scopolamine patches; no opioid medications within 24 hours of study drug administration; no use of an investigational product within 30 days or 5 elimination half-lives of such investigational drug, whichever was longer, prior to study drug administration, or planned administration of another investigational product or procedure during the subject's participation in this study was not permitted; no drugs (other than the described bupivacaine HCl admixture) were to be admixed with study drug (e.g., epinephrine, dexamethasone, clonidine); no lidocaine or other local anesthetics were locally administered in the area of the nerve block administration other than use in a superficial cutaneous wheal for needle insertion.

Perioperative treatment may include receiving an IPACK infiltration under ultrasound guidance with 15 mL (37.5 mg) 0.25% bupivacaine HCl immediately following study drug administration (was to be done with the same set-up for the nerve block); receiving spinal anesthesia immediately prior to surgery with 0.5% bupivacaine HCl (≥15 mg). If the spinal failed or could not be completed, the subject may have received total intravenous anesthesia; receiving 1000 mg of IV acetaminophen at the time of surgical incision; receiving propofol for induction and intra-operative sedation. Other permitted medications may include tranexamic acid. Restricted medications included no other medication (including opioids) were to be mixed with the bupivacaine for spinal anesthesia; no use of dexamethasone, acetaminophen/paracetamol, ketorolac, or other NSAIDs preemptively or intra operatively, except for emergency use to treat an AE; no intra operative use of opioids (except IV fentanyl at a dose not exceeding 1 μg/kg, unless deemed medically necessary) and ketamine.

Post-surgical treatment may include receiving 1 postoperative dose of 1000 mg IV acetaminophen, administered approximately 8 hours after the first dose (approximately 8 hours after incision), maximum total dose was not to exceed 2000 mg; no additional acetaminophen was permitted after the second IV acetaminophen dose. Other permitted medications may include ondansetron or metoclopramide could be used for postoperative nausea and vomiting. Restricted medications included no other analgesics, including fentanyl, within 96 hours after surgery, no scopolamine patches; no patient controlled analgesia; no dexmedetomidine HCl (Precedex®) use; no lidocaine (except, if used as a local anesthetic at the site of IV placement) or other local anesthetics to be locally administered in the area of the nerve block administration through POD7; systemic glucocorticosteroids and neuromodulating agents (e.g., gabapentin, pregabalin [Lyrica®], duloxetine [Cymbalta®], etc.).

An unscheduled pain intensity assessment using the NRS (measured as "On a scale from 0 to 10, where 0 equals no pain and 10 equals the worst possible pain, how much pain are you experiencing in your operative knee right now?") was to be completed immediately prior to administration of any breakthrough pain medication up to 96 hours post-surgery. Medications were administered as needed; opioids were not to be given on a pre-determined schedule. Immediate release PO oxycodone could be administered in a stepwise approach as follows: initial dose of 5 mg oxycodone offered; if the initial opioid dose was insufficient for pain relief, an additional 5 mg oxycodone could be offered up to a maximum of 10 mg (total dose); if a subject was unable to tolerate PO medication or the PO oxycodone pain relief was insufficient, IV morphine (initiated at 2 mg) or hydromorphone (initiated at 0.2 mg) could be administered. No NSAIDs or other opioids, including tramadol were allowed for breakthrough pain management. No acetaminophen (other than the scheduled IV acetaminophen) was to be used for breakthrough pain. Pain management modalities were standardized during the first 96 hours post-surgery. After 96 hours, the analgesic regimen could be adjusted for each subject individually as deemed appropriate by the physician responsible for the postsurgical care.

All postsurgical analgesics administered, were to be recorded through hospital discharge.

Efficacy assessments included pain intensity scores focused on the operative knee using the Numeric Rating Scale (NRS), total postsurgical opioid consumption in OMED, time to first opioid consumption post-surgery, and subject satisfaction using the International Pain Outcome (IPO). Additionally, blood samples for PK analysis (area under the curve [AUC], maximum plasma concentration [Cmax], time of maximum plasma concentration [Tmax], including early and late Cmax and Tmax (EXP133-ADMIX arm only), apparent terminal elimination half-life [t½e1], apparent clearance [CL/F], and apparent volume of distribution [Vd/F]) and PD assessment data (sensory and motor block) were collected from Cohort 1 subjects.

Safety assessments included monitoring of AEs (including SAEs and adverse events of special interest [AESIs]), vital signs (temperature, resting heart rate, respiratory rate, oxygen saturation, and blood pressure), 12 lead EKG, and recording of concomitant medications.

The Screening Visit was conducted within 45 days prior to study drug administration and the time from study drug administration until the end of participation was post-operative day (POD) 14 (±3 days), at which time a final follow up telephone call occurred. Therefore, the total duration of participation in the study for subjects was up to 62 days.

End Points

The primary endpoint was the AUC of the NRS pain intensity scores from 0 to 96 hours post-surgery.

Secondary efficacy endpoints included total postsurgical opioid consumption in OMED from 0 to 96 hours post-surgery; time to first opioid consumption post-surgery; and worst and average NRS pain intensity scores at 24, 48, 72, and 96 hours post-surgery.

Exploratory efficacy endpoints included opioid-free status from 0 to 24, 48, 72, and 96 hours post-surgery; subject satisfaction as measured by IPO at 96 hours post-surgery; AUC of "average" pain scores from POD1 through POD4; AUC of "worst" pain scores from POD1 through POD4; and current pain intensity scores from 0 to 96 hours post-surgery.

Safety endpoints included incidence of treatment emergent adverse events and SAEs from start of the nerve block procedure through POD14; change from baseline in vital signs over time; and abnormal post-baseline EKG findings.

Pharmacokinetic endpoints included area under the plasma concentration-versus-time curve, specifically from the time of dosing to the time of the last quantifiable concentration (AUC0-last) and AUC from the time of dosing to infinity (AUC0-∞); maximum plasma concentration (Cmax) and time of maximum plasma concentration (Tmax) for subjects treated with bupivacaine HCl; early and late Cmax and Tmax were determined for subjects treated with EXPAREL admixed with bupivacaine HCl (EXP133-ADMIX arm); t½el; CL/F; Vd/F.

Pharmacodynamic endpoints included: duration of the sensory block and motor block; time to onset of sensory block and motor block; and time to offset of sensory block and motor block.

| Pharmacokinetic Parameters | |
|---|---|
| Parameter | Definition |
| $C_{max}^1$ | The maximum observed plasma concentration obtained directly from the concentration-time data |
| Early $C_{max}^2$ | The maximum observed plasma concentration occurring between dosing (0 h) and x h after dosing if appropriate based on the individual subject and treatment arm mean concentration-time plots, where x was determined from the concentration-time plot |
| Late $C_{max}^2$ | The maximum observed plasma concentration occurring more than x h after dosing if appropriate based on the individual subject and treatment arm mean concentration-time plots, where x was a subject-specific local minimum turning point in the concentration-time curve |
| $T_{max}^1$ | Time at which $C_{max}$ was observed |
| Early $T_{max}^2$ | Time at which early $C_{max}$ was observed |
| Late $T_{max}^2$ | Time at which late $C_{max}$ was observed |
| $\lambda_z$ | The apparent terminal elimination rate constant was estimated at the terminal phase by linear regression after log-transformation of the concentrations |
| $t_{1/2el}$ | The apparent terminal elimination half-life was calculated as $\ln(2)/\lambda_z$ |
| $C_t$ | The last quantifiable concentration |
| $AUC_{0\text{-}last}$ | The area under the plasma concentration-time curve from the time of dosing to the time of the last quantifiable concentration; calculated using the linear-up/log-down trapezoidal method |
| $AUC_{0\text{-}\infty}$ | The area under the plasma concentration-time curve from the time of dosing (zero) to infinity; calculated as the sum of $AUC_{0\text{-}last}$ and residual area $C_t/\lambda_z$ |
| $AUC_{extr}$ | Extrapolated area under the curve from time of last point above LLOQ to infinity, expressed as percentage of $AUC_{0\text{-}\infty}$; calculated as $(C_t/\lambda_z)/AUC_{0\text{-}\infty} \times 100\%$. |
| CL/F | Apparent clearance was estimated as dose/$AUC_{0\text{-}\infty}$, with doses calculated as follows (note that every subject received 37.5 mg bupivacaine HCl during IPACK): EXP133-ADMIX arm = 133 + ([50 + 37.5] × 0.8867) = 210.6 mg BUP50 arm = (50 + 37.5 mg) × 0.8867 (salt to free base conversion) = 77.6 mg |
| $V_d/F$ | Apparent volume of distribution was estimated as (CL/F)/$\lambda_z$ |

Abbreviations: HCL = hydrochloride; IPACK = infiltration between the popliteal artery and capsule of the knee; LLOQ = lower limit of quantitation.
[1]Calculated for BUP50 arm only.
[2]Calculated for EXP133-ADMIX arm only.

Statistical Analysis

Descriptive statistics (number of subjects, mean, standard deviation [SD], median, minimum, and maximum) were provided for continuous data. Tabulations (number and percentage of subjects) by category were provided for categorical data. Unless specified otherwise, all confidence intervals (CIs) were 2-sided with 95% confidence. All hypothesis tests were between the select EXPAREL dose group and the bupivacaine HCl group. All statistical comparisons were 1-sided tests at an alpha level of 0.025.

The AUC of NRS pain intensity scores from 0-96 hours post-surgery were analyzed using the analysis of covariance (ANCOVA) model. The main contrast of interest to assess treatment effect was the difference between treatment arms in the AUC of pain score's least square means.

Total postsurgical opioid consumption in OMED from 0 to 96 hours was analyzed using an ANCOVA model. Time to first postsurgical opioid medication was analyzed using the Kaplan Meier survival method. Worst and average NRS pain intensity scores through 24 h, 48 h, 72 h, and 96 hours from the end of surgery were summarized by treatment arm.

To control for the overall Type-I error rate for the multiple comparisons in the efficacy analyses, the statistical tests were conducted in a hierarchical order as follows:

1. Primary endpoint (AUC of NRS pain 0 to 96 hours post-surgery).
2. First secondary endpoint (Total postsurgical opioid dose 0 to 96 hours).
3. Second secondary endpoint (Time to first postsurgical opioid).
4. Third secondary endpoint (worst and average NRS pain intensity scores at 24, 48, 72, and 96 hours post-surgery).

At any step, if the statistical test became non-significant, all the subsequent tests were deemed non-significant.

Adverse events and SAEs were recorded from the time of informed consent through POD14. Adverse events were coded using the Medical Dictionary for Regulatory Activities version 24.1 and summary tables were based on the Safety Analysis Set. A subject data listing was provided for all AEs, which included the reported term, preferred term, system organ class, treatment-emergent adverse event flag, study day of AE onset, AE start/stop date and time, relationship to study drug, frequency, severity, action taken with subject, outcome, and seriousness criteria.

Vital signs and their change from baseline were summarized with mean, median, and standard deviation at baseline and at each scheduled time point. The frequency and percentage of EKG findings (normal, abnormal/not clinically significant, and abnormal/clinically significant) were summarized at screening and each scheduled time point.

An interim analysis was conducted to evaluate sample size assumptions and futility. The interim analysis was conducted when a total of 80 subjects (40 subjects in each arm) combined from either Cohort 1 or Cohort 2 were enrolled and provided complete assessment data for the primary efficacy outcome.

Results

Efficacy

From 0 to 96 hours post-surgery, subjects in the EXP133 ADMIX arm had a lower mean AUC of NRS Pain Intensity Score compared with the BUP50 arm with an LSM difference of −65.8 (95% CI=−118.7, −12.9; p=0.0074). The EXP133 ADMIX arm had significantly lower mean AUC of NRS Pain Intensity Scores than the BUP50 arm, particularly after the first 24 hours post-surgery (LSM difference range=−55.9 to 10.0; p values ≤0.0404).

For all time intervals in the first 96 hours post-surgery, subjects in the EXP133 ADMIX arm had a lower total opioid consumption compared with the BUP50 arm with LSM ratios over bupivacaine ranging from 0.72 to 0.83; this was particularly evident in the first 48 hours post-surgery (p-values ≤0.0201).

All subjects took opioid rescue medication. The median time to first rescue medication was 4.15 hours (95% CI=3.80, 4.83) for the EXP133-ADMIX arm and 3.63 hours (95% CI=2.98, 4.05) for those in the BUP50 arm, with a hazard ratio of 0.70 (95% CI=0.51, 0.96; 1-sided p-value=0.0127; 2 sided p value=0.0578).

Mean worst pain intensity was significantly lower for the EXP133 ADMIX arm compared with the BUP50 arm on Day 3 (LSM difference [SE]=−0.7 [0.34]; p=0.0215). The mean average pain intensity was significantly lower for the EXP133 ADMIX arm compared with the BUP50 arm on Days 2 and 3 (LSM difference [SE]=0.6 [0.28] and −0.5 [0.31], respectively; p values ≤0.0476).

From 0 to 24 h, 1.2% of subjects from the EXP133-ADMIX arm were opioid-free. At all other time intervals (0 to 48/72/96 hours post-surgery), no subjects were opioid-free. No subjects in the BUP50 arm were opioid free at any time interval up to 96 hours post-surgery.

Mean subject satisfaction between the EXP133-ADMIX arm (mean [SD]=8.1 [2.47]) and the BUP50 arm (mean [SD]=8.1 [2.16]) was similar (LSM difference [SE]=0.0 [0.36]; p=0.4608) at 96 hours post-surgery.

Mean AUC of worst and average pain over the last 24 hours post-surgery from POD 1 through POD 4 were significantly different (p-values ≤0.0270) between the EXP133 ADMIX arm and BUP50 arm with 6.09% and 8.97% lower values in the EXP133-ADMIX arm, respectively.

The mean current pain intensity post-surgery peaked at 24 hours post-surgery, gradually decreasing until 96 hours post-surgery in both treatment arms. From 24 hours until 54 hours post-surgery, the EXP133-ADMIX arm had a significantly lower LSM compared with the BUP50 arm at all time points (p values ≤0.0269).

In the EXP133-ADMIX arm, mean peak PK concentration was best described by an early and a late Cmax. The mean early Cmax was 467.04 ng/mL, occurring at a median time of 0.63 hours post-dose; this aligned well with the BUP50 arm, which had a Cmax of 333.89 ng/mL at a median time of 0.65 h. The mean late Cmax in the EXP133 ADMIX arm was 334.79 ng/mL, occurring at a median time of 60.94 h; by comparison, the mean bupivacaine concentration at 60 hours in the BUP50 arm was 43.25 ng/mL.

Mean extent of exposure as described by AUC0-last and AUC0-∞ were 25038.63 h×ng/mL and 25109.09 h×ng/mL in the EXP133-ADMIX arm, respectively and 7283.31 h×ng/mL and 7446.40 h×ng/mL (3510.207) in the BUP50 arm. The mean t½e1, CL/F, and Vd/F values were similar between treatment arms.

In both treatment arms, the first time point at which knee extension was not present in the majority of subjects (EXP133 ADMIX: 58.3%; BUP50: 71.4%) was 8 hours post dose.

The median duration of sensory block was about 2-fold longer in the EXP133-ADMIX arm (22.90 hours) compared with the BUP50 arm (11.63 hours). However, difference comparisons versus bupivacaine for the duration of sensory block did not achieve statistical significance (p-values ≥0.1222). Sensory block was observed in ≥50% of subjects in each treatment arm at 30 min post dose. All subjects in the BUP50 arm regained normal sensory function by 24 hours post-dose, whereas, this was not attained by all EXP133 ADMIX subjects until 144 hours post dose.

Safety

No deaths occurred during this study and EXPAREL admixed with bupivacaine HCl was well tolerated by subjects.

A similar proportion of subjects had ≥1 TEAE in each treatment arm (EXP133-ADMIX: 89.5%; BUP50: 88.8%). The most commonly reported TEAEs overall were nausea (38.6%), constipation (36.7%), muscle spasms (12.0%), and insomnia (10.8%), with all other TEAEs being reported in <10% of subjects.

Five (3.0%) subjects had ≥1 TEAE related to study drug, with 3 subjects in the EXP133 ADMIX arm and 2 subjects in the BUP50 arm. Related TEAEs included hypokalemia, hyponatraemia, confusional state, tachycardia, and muscle spasms (1 subject each), and procedural pain (2 subjects).

Overall, TEAEs were mostly mild; 102 (61.4%) subjects had a highest severity grade of mild, 43 (25.9%) subjects had moderate TEAEs, and 3 (1.8%) subjects had severe TEAEs. The proportion of subjects with moderate and severe TEAEs were similar between treatment arms. Severe TEAEs included muscle spasms (3 subjects) and pulmonary embolism (1 subject).

Four (2.4%) subjects had AESIs that included a fall, post procedural haematoma, and dizziness (2 subjects).

Six (3.6%) subjects had ≥1 SAE, with 3 subjects in each treatment arm. All SAEs were assessed as not related or unlikely related to the study drug and included a post procedural haematoma, pneumonia, acute myocardial infarction, atrial fibrillation, pulmonary embolism, and angioedema.

One subject in the BUP50 arm that discontinued from the study following SAEs of acute myocardial infarction and atrial fibrillation.

There were minimal changes in vital signs and values were similar between treatment arms. Small decreases following surgery were noted in systolic blood pressure, diastolic blood pressure, and heart rate.

From Screening to POD7, scheduled EKG assessments were normal or not clinically significant for most subjects, with only 3 subjects (2 in EXP133-ADMIX, 1 in BUP50) having clinically significant abnormal EKG findings at 1 time point each.

Summary of Results and Conclusions

Following surgery, subjects in the EXP133 ADMIX arm had less pain severity and lower total opioid consumption.

The median time to first rescue medication was significantly longer (4.15 hours vs. 3.63 hours) for the EXP133 ADMIX arm compared with the BUP50 arm.

In the EXP133-ADMIX arm, mean peak PK concentrations occurred at median times of 0.63 hours and 60.94 h, supporting prolonged pain control in those that received the study drug. In the BUP50 arm, a single peak PK concentration occurred at a median time of 0.65 h.

Peak bupivacaine concentrations in the EXP133-ADMIX arm and BUP50 arm aligned well with the return of motor and sensory function and suggest a prolonged analgesic effect of EXPAREL admixed with bupivacaine HCl compared with bupivacaine HCl alone. All motor and sensory function returned to normal by 168 hours post dose in both treatment arms.

No deaths occurred during this study and EXPAREL admixed with bupivacaine HCl was well tolerated by subjects.

A similar proportion of subjects had ≥1 TEAE in each treatment arm (EXP133-ADMIX: 89.5%; BUP50: 88.8%). Five (3.0%) subjects had ≥1 TEAE related to study drug, with 3 subjects in the EXP133 ADMIX arm and 2 subjects in the BUP50 arm. Six (3.6%) subjects had ≥1 SAE, with 3 subjects in each treatment arm.

Adverse Events

An AE can be defined as any untoward medical occurrence associated with the use of a drug in humans, whether or not considered drug related. An AE (also referred to as an adverse experience) could be any unfavorable and unintended sign (e.g., abnormal laboratory finding), symptom, or disease temporally associated with the use of a drug, without any judgment about causality. An AE could arise from any use of the drug (e.g., off-label use in combination with another drug) and from any route of administration, formulation, or dose, including an overdose.

An AE could be any unfavorable and unintended change in a body structure or body function. Adverse events included any clinically significant deterioration of a subject's medical status. The AE could involve any organ or system and could be represented by the new onset or deterioration of a disease, syndrome, symptom, or physical sign, as well as by findings and results of instrumental examinations and laboratory tests. Any medically relevant and untoward change after the subject signed the ICF, including frequency or pattern changes for a fluctuating condition (e.g., migraine), was considered an AE.

An AE that occurred after administration of the study treatment was considered a treatment-emergent adverse event (TEAE). A continuous AE with varying grades of severity was to be recorded as 1 AE. The highest grade of severity experienced by that subject during the course of the continuous AE was to be recorded.

In general, the severity of an AE was to be categorized using the following guidelines:

Mild: An AE that was easily tolerated by the subject, caused minimal discomfort, and did not interfere with everyday activities.

Moderate: An AE that was discomforting and interfered with normal everyday activities.

Severe: An AE that prevented normal everyday activities.

Assessment of the relationship of the AE to study drug after careful medical consideration on a case-by-case basis. General guidelines are provided below:

Unrelated: A causal relationship between the study drug and the AE could be easily ruled out (e.g., based on the temporal sequence, absence of a reasonable pathophysiological mechanism, or direct evidence of actual cause).

Unlikely: A clinical event with a temporal relationship to study drug administration that made a causal relationship improbable and in which other drugs, chemicals, or underlying disease provided a plausible explanation.

Possible: A clinical event with a reasonable time sequence to administration of the study drug but that could also be explained by a concurrent disease or other drugs or chemicals.

Probable: A clinical event with a reasonable time sequence to administration of the study drug unlikely to be attributed to a concurrent disease or other drugs or chemicals and that followed a clinically reasonable response on withdrawal (dechallenge).

Definite: The pharmacological properties of the study drug(s) or of the substance class, and the course of the AE after dechallenge and, if applicable, after rechallenge, and/or specific test indicated involvement of the study drug(s) in the occurrence/worsening of the AE, and no indication of other causes existed.

Based on review of all peripheral nerve blocks, the following conditions were considered to be Adverse Events of Special Interest (AESIs) upon review of the AEs:

Falls
Persistent tingling
Persistent numbness
Persistent weakness
Hypersensitivity
Seizures
Tremors
Dizziness
Hematoma formation
Cardiovascular depression
Dyspnea
Cardiovascular arrest
Altered sensorium
Visual disturbances
Local anesthetic systemic toxicity Adverse events of special interest classified as persistent referred to any condition (e.g., tingling, numbness, or sensory/motor weakness that affected the nerve block region, after the study drug administration) that persisted for >168 h from the time of onset.

A Serious Adverse Event (SAE) was defined as an AE or suspected adverse reaction that, in the view of either the Investigator or Sponsor, resulted in any of the following outcomes:

Death: Any event that resulted in a subject's death was reported as an SAE. However, death, in and of itself, was not an AE; it was an outcome. The cause of death was the AE. Therefore, the Investigator was to make every effort to obtain and document the cause of death for all subjects who died during the study. If, despite all efforts, the cause of death remained unknown, the AE was to be documented as an "unspecified fatal event."

Life-threatening: An AE was considered life-threatening if, in the view of either the Investigator or Sponsor, its occurrence placed the subject at immediate risk of death. It did not include an AE that, had it occurred in a more severe form, might have caused death.

Inpatient hospitalization or prolongation of existing hospitalization: Hospitalization, in and of itself, did not represent an SAE. It was the AE leading to the subject's hospitalization that became "serious" when it required inpatient care. Consequently, an SAE was not to be reported in case of preplanned hospitalizations for a pre-existing condition that did not worsen during the study. However, any medical condition that delayed a subject's discharge from the hospital (i.e., prolonged hospitalization) or required the subject to be readmitted was reported as an SAE.

Persistent or significant incapacity: A substantial disruption of a person's ability to conduct normal life functions.

Congenital anomaly/birth defect: If suspected that exposure to the study drug prior to conception or during pregnancy may have resulted in an adverse outcome in the child.

Medically significant: Important medical events that did not result in death, were not life-threatening, or did not require hospitalization, could be considered serious when, based upon appropriate medical judgment, they could jeopardize the subject and might have required medical or surgical intervention to prevent one of the outcomes listed in this definition.

Any SAE or death that occurred at any time after the subject signed the ICF through POD14, whether or not related to study drug, was to be reported within 24 h of discovery.

The invention claimed is:

1. A method of administering regional analgesia by adductor canal block to a patient, the method comprising:
   a) selecting an entry point of an injection needle in a leg of a patient by ultrasound transducer;
   b) inserting the injection needle into the patient at the entry point;
   c) identifying a first nerve in the adductor canal of the leg of the patient;
   d) administering to the first nerve saline and a pharmaceutical composition;
   e) identifying a second nerve in the adductor canal of the leg of the patient;
   f) administering to the second nerve saline and the pharmaceutical composition, wherein 133 mg of the pharmaceutical composition is administered in total;
   wherein the first nerve and second nerve are selected from the group consisting of the nerve to vastus medialis (NVM) and the saphenous nerve, and wherein the first nerve is not the second nerve, and
   wherein the pharmaceutical composition comprises multivesicular liposomes comprising: at least one amphipathic lipid, at least one neutral lipid, and bupivacaine phosphate, wherein the bupivacaine phosphate is encapsulated within the multivesicular liposome,
   thereby administering regional analgesia by adductor canal block to the patient.

2. The method of claim 1, wherein the injection needle is connected to a peripheral nerve stimulator (PNS).

3. The method of claim 2, wherein the PNS is used to identify the first nerve and/or the second nerve.

4. The method of claim 1, wherein the injection needle is a 100 mm, 21-gauge needle.

5. The method of claim 1, wherein administering the pharmaceutical composition comprises administering about 10 mL of the pharmaceutical composition to each of the first nerve and the second nerve.

6. The method of claim 1, wherein the method comprises administering about 20 mL total of the pharmaceutical composition.

7. The method of claim 1, wherein the multivesicular liposomes comprise:
   bupivacaine or a salt thereof;
   phosphoric acid;
   a lipid component comprising at least one amphipathic lipid and at least one neutral lipid lacking a hydrophilic head group; and,
   a cholesterol and/or a plant sterol,
   wherein said multivesicular liposomes are made by a process comprising:
      a) preparing a first aqueous component comprising phosphoric acid;
      b) preparing a lipid component comprising at least one organic solvent, at least one amphipathic lipid, and at least one neutral lipid lacking a hydrophilic head group;
      c) mixing said first aqueous component and said lipid component to form a water-in-oil emulsion, wherein at least one component of the lipid component and the first aqueous component comprises bupivacaine or a salt thereof;
      d) mixing said water-in-oil emulsion with a second aqueous component to form solvent spherules; and
      e) removing the organic solvent from the solvent spherules to form multivesicular liposomes encapsulating bupivacaine phosphate.

8. The method of claim 1, further comprising administering local anesthetic to the patient in the space between the popliteal artery and the posterior capsule of the knee.

9. A method of reducing opioid consumption over a period of at least 24 hours, the method comprising:
   a) selecting an entry point of an injection needle in a leg in a patient by ultrasound transducer;
   b) advancing a needle tip of the injection needle within a region between a vastus medialis muscle and a sartorius muscle of the patient along a trajectory that extends between the entry point and a superficial femoral artery;
   c) identifying a first nerve in the adductor canal of the leg of the patient;
   d) administering to the first nerve through the injection needle saline and about 10 mL of a pharmaceutical composition;
   e) identifying a second nerve in the adductor canal of the leg of the patient;
   f) administering to the second nerve through the injection needle saline and about 10 mL of the pharmaceutical composition, wherein 133 mg of the pharmaceutical composition is administered in total;
   wherein the first nerve and second nerve are selected from the group consisting of the nerve to vastus medialis (NVM) and the saphenous nerve, and wherein the first nerve is not the second nerve, and
   wherein the pharmaceutical composition comprises multivesicular liposomes comprising: at least one amphipathic lipid, at least one neutral lipid, and bupivacaine phosphate, wherein the bupivacaine phosphate is encapsulated within the multivesicular liposome,
   thereby reducing opioid consumption over a period of at least 24 hours.

10. The method of claim 9, wherein the injection needle is connected to a peripheral nerve stimulator (PNS).

11. The method of claim 10, wherein the PNS is used to identify the first nerve and/or the second nerve.

12. The method of claim 9, wherein the injection needle is a 100 mm, 21-gauge needle.

13. The method of claim 9, wherein the multivesicular liposomes comprise:
bupivacaine or a salt thereof;
phosphoric acid;
a lipid component comprising at least one amphipathic lipid and at least one neutral lipid lacking a hydrophilic head group; and,
a cholesterol and/or a plant sterol,
wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component of the lipid component and the first aqueous component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

14. The method of claim 9, further comprising administering local anesthetic to the human patient in the space between the popliteal artery and the posterior capsule of the knee.

15. The method of claim 14, wherein the local anesthetic comprises bupivacaine HCl.

16. The method of claim 14, wherein the space between the popliteal artery and the posterior capsule of the knee is determined by ultrasound.

17. A method of administering an adductor canal block to a patient, the method comprising:
a) selecting an entry point of an injection needle in a leg of the patient;
b) inserting the injection needle into the leg of the patient at the entry point;
c) identifying a first nerve in the adductor canal of the leg of the patient;
d) administering to the first nerve a pharmaceutical composition;
e) identifying a second nerve in the adductor canal of the leg of the patient;
f) administering to the second nerve the pharmaceutical composition wherein 133 mg of the pharmaceutical composition is administered in total;
wherein the first nerve and second nerve are selected from the group consisting of the nerve to vastus medialis (NVM) and the saphenous nerve, and wherein the first nerve is not the second nerve, and
wherein the pharmaceutical composition comprises multivesicular liposomes comprising: at least one amphipathic lipid, at least one neutral lipid, and bupivacaine phosphate, wherein the bupivacaine phosphate is encapsulated within the multivesicular liposome, thereby administering the adductor canal block to the patient.

18. The method of claim 17, wherein the needle is connected to a peripheral nerve stimulator (PNS), which is tuned to 2 hertz and between 0.5 to 1.0 mA.

19. The method of claim 18, wherein the PNS is used to identify the first nerve and/or the second nerve.

20. The method of claim 17, wherein the injection needle is a 100 mm, 21-gauge needle.

21. The method of claim 17, wherein inserting the injection needle into the leg of the patient comprises advancing a needle tip of the injection needle within a region between a vastus medialis muscle and a sartorius muscle of the patient along a trajectory that extends between the entry point and a superficial femoral artery.

22. The method of claim 17, wherein the multivesicular liposomes comprise:
bupivacaine or a salt thereof;
phosphoric acid;
a lipid component comprising at least one amphipathic lipid and at least one neutral lipid lacking a hydrophilic head group; and,
a cholesterol and/or a plant sterol,
wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component of the lipid component and the first aqueous component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

23. The method of claim 17, wherein administering the pharmaceutical composition comprises administering about 10 mL of the pharmaceutical composition to each of the first nerve and the second nerve.

24. The method of claim 17, wherein the method comprises administering about 20 mL total of the pharmaceutical composition.

25. The method of claim 17, further comprising administering local anesthetic to the patient in the space between the popliteal artery and the posterior capsule of the knee.

26. A method of increasing the amount of time before opioid medication is administered to a patient, the method comprising:
a) selecting an entry point of an injection needle in a leg of a patient by ultrasound transducer, wherein the entry point comprises a region adjacent to a superficial femoral artery in the middle of a sartorius muscle;
b) advancing a needle tip of the injection needle within a region between a vastus medialis muscle and a sartorius muscle of the patient along a trajectory that extends between the entry point and a superficial femoral artery;
c) identifying a nerve to vastus medialis (NVM) in the patient;
d) administering to the NVM through the injection needle about 10 mL of a multivesicular liposome pharmaceutical composition;

e) identifying a saphenous nerve, wherein identifying a saphenous nerve in the patient comprises penetrating a vasto-adductor membrane with the needle tip and advancing the needle tip to a location anterior to the superficial femoral artery;
f) administering to the saphenous nerve through the injection needle about 10 mL of a multivesicular liposome pharmaceutical composition to the saphenous nerve, wherein 133 mg of the pharmaceutical composition is administered in total;

wherein the multivesicular liposome pharmaceutical composition comprises:

bupivacaine or a salt thereof;

phosphoric acid;

a lipid component comprising at least one amphipathic lipid and at least one neutral lipid lacking a hydrophilic head group; and, a cholesterol and/or a plant sterol, thereby increasing the amount of time before opioid medication is administered to the patient.

27. The method of claim 26, wherein the needle is connected to a peripheral nerve stimulator (PNS), which is tuned to 2 hertz and between 0.5 to 1.0 mA.

28. The method of claim 26, further comprising administering local anesthetic to the patient in the space between the popliteal artery and the posterior capsule of the knee.

* * * * *